US012599698B2

(12) United States Patent
Drake

(10) Patent No.: US 12,599,698 B2
(45) Date of Patent: *Apr. 14, 2026

---

(54) THERAPEUTIC ARTICLE OF MANUFACTURE WITH NANOPARTICLES TO PROMOTE WOUND HEALING AND/OR ANTIMICROBIAL INFECTION CONTROL

(71) Applicant: KISMET TECHNOLOGIES LLC, Winter Park, FL (US)

(72) Inventor: Christina H. Drake, Winter Park, FL (US)

(73) Assignee: Kismet Technologies Inc., Orlando, FL (US)

( * ) Notice: Subject to any disclaimer, the term of this patent is extended or adjusted under 35 U.S.C. 154(b) by 647 days.

This patent is subject to a terminal disclaimer.

(21) Appl. No.: 17/973,769

(22) Filed: Oct. 26, 2022

(65) Prior Publication Data

US 2023/0137248 A1 May 4, 2023

Related U.S. Application Data

(60) Provisional application No. 63/272,930, filed on Oct. 28, 2021.

(51) Int. Cl.

| | |
|---|---|
| *A61L 26/00* | (2006.01) |
| *A61K 9/14* | (2006.01) |
| *A61K 33/00* | (2006.01) |
| *A61K 33/24* | (2019.01) |
| *A61K 33/242* | (2019.01) |
| *A61K 33/243* | (2019.01) |
| *A61K 33/26* | (2006.01) |
| *A61K 33/30* | (2006.01) |
| *A61K 33/34* | (2006.01) |
| *A61K 33/38* | (2006.01) |
| *A61K 38/19* | (2006.01) |
| *A61K 47/10* | (2017.01) |
| *A61K 47/34* | (2017.01) |
| *A61K 47/36* | (2006.01) |
| *A61K 47/42* | (2017.01) |
| *A61K 48/00* | (2006.01) |
| *A61P 27/02* | (2006.01) |

(52) U.S. Cl.
CPC ............ *A61L 26/0066* (2013.01); *A61K 9/14* (2013.01); *A61K 33/00* (2013.01); *A61K 33/24* (2013.01); *A61K 33/242* (2019.01); *A61K 33/243* (2019.01); *A61K 33/26* (2013.01); *A61K 33/30* (2013.01); *A61K 33/34* (2013.01); *A61K 33/38* (2013.01); *A61K 38/19* (2013.01); *A61K 47/10* (2013.01); *A61K 47/34* (2013.01); *A61K 47/36* (2013.01); *A61K 47/42* (2013.01); *A61L 26/0095* (2013.01); *A61P 27/02* (2018.01); *A61K 48/00* (2013.01); *A61L 2300/104* (2013.01); *A61L 2300/402* (2013.01); *A61L 2300/404* (2013.01); *A61L 2300/41* (2013.01); *A61L 2400/12* (2013.01)

(58) Field of Classification Search
CPC ........ A61K 33/00; A61K 9/14; A61K 9/0014; B82Y 30/00
See application file for complete search history.

(56) References Cited

U.S. PATENT DOCUMENTS

| | | |
|---|---|---|
| 4,826,893 A | 5/1989 | Yamazaki et al. |
| 4,866,042 A | 9/1989 | Neuwelt |
| 5,223,425 A | 6/1993 | Flier et al. |
| 5,290,552 A | 3/1994 | Sierra et al. |
| 5,464,764 A | 11/1995 | Capecchi et al. |
| 5,487,992 A | 1/1996 | Capecchi et al. |
| 5,947,917 A * | 9/1999 | Carte .................. A61F 13/0253 |
| | | 602/58 |
| 7,638,484 B2 | 12/2009 | Braiman-Wilksman et al. |
| 8,400,408 B2 | 3/2013 | Hotelling et al. |
| 8,507,431 B2 | 8/2013 | Braiman-Wilksman et al. |
| 10,155,361 B2 | 12/2018 | Bookbinder et al. |
| 10,289,225 B2 | 5/2019 | Jin et al. |
| 10,642,426 B2 | 5/2020 | Hwang et al. |

(Continued)

FOREIGN PATENT DOCUMENTS

| | | |
|---|---|---|
| CA | 2644315 | 10/2007 |
| CN | 102559138 | 11/2012 |

(Continued)

OTHER PUBLICATIONS

Neal et al (ACS Nano, Aug. 2021, vol. 15, pp. 14544-14556) (Year: 2021).*

Neal, Craig J. et al., "schemMetal-Mediated Nanoscale Cerium Oxide Inactivates Human Coronavirus and Rhinovirus , by Surface Disruption," ACS Nano, 2021, 15(9), 14544-14556. doi: 10.1021/acsnano.1c04142.

Szczesio-Wlodarczyk, A. et al., "An Evaluation of the Properties of Urethane Dimethacrylate-Based Dental Resins," Materials, 2021, 14(11):2727. https://doi.org/10.3390/ma14112727.

(Continued)

*Primary Examiner* — Mark V Stevens
(74) *Attorney, Agent, or Firm* — Terry M. Sanks, Esq.; Beusse Sanks, PLLC

(57) ABSTRACT

A therapeutic article of manufacture that includes a body having fibers treated with a mixture including metal-modified cerium oxide nanoparticles (mCNPs) and one or more of a polymeric binder, a dispersant and a stabilizer. The mCNPs have a predominant 3+ surface charge and in a range of about 3-35 nanometers (nm) in size. The mCNPs are mixed in an amount that is in a range of about 0.01 to 0.1 weight percentage of the mixture having the mCNPs and the one or more of a polymeric binder, a dispersant and a stabilizer. The metal (m) is an antimicrobial promoting metal that is non-ionizing. A method is also provided that promotes wound healing and/or antimicrobial infection control with a barrier of the therapeutic article of manufacture.

19 Claims, 7 Drawing Sheets

(56) References Cited

U.S. PATENT DOCUMENTS

| | | | |
|---|---|---|---|
| 10,925,773 | B2 | 2/2021 | Riesinger |
| 2006/0155041 | A1 | 7/2006 | Suzuki et al. |
| 2007/0000407 | A1 | 1/2007 | Leong |
| 2009/0130157 | A1 | 5/2009 | Ylitalo et al. |
| 2011/0002971 | A1 | 1/2011 | Hassler et al. |
| 2011/0038909 | A1 | 2/2011 | Roe et al. |
| 2012/0020917 | A1 | 1/2012 | Braiman-Wiksman et al. |
| 2012/0107556 | A1 | 5/2012 | Zhang et al. |
| 2012/0181177 | A1 | 7/2012 | Yu et al. |
| 2012/0328681 | A1* | 12/2012 | Hassler .................. D06M 11/45 |
| | | | 977/773 |
| 2013/0115441 | A1 | 5/2013 | Bookbinder et al. |
| 2013/0195927 | A1 | 8/2013 | Sudipta et al. |
| 2013/0211028 | A1 | 8/2013 | Shinike et al. |
| 2016/0158403 | A1 | 6/2016 | Watson |
| 2016/0194503 | A1 | 7/2016 | Karl |
| 2017/0202965 | A1 | 7/2017 | Baker |
| 2017/0252320 | A1 | 9/2017 | Martins-Green et al. |
| 2018/0028431 | A1 | 2/2018 | Chiattello et al. |
| 2018/0110658 | A1 | 4/2018 | Lin |
| 2018/0339913 | A1 | 11/2018 | Seal et al. |
| 2019/0111424 | A1 | 4/2019 | Chou et al. |
| 2019/0262393 | A1 | 8/2019 | Pesavento |
| 2019/0275195 | A1* | 9/2019 | Leibler ............... A61L 26/0066 |

FOREIGN PATENT DOCUMENTS

| | | |
|---|---|---|
| WO | 2005013885 | 2/2005 |
| WO | 101138342 | 5/2011 |
| WO | 2017011886 | 1/2017 |
| WO | 2021222779 | 11/2021 |

OTHER PUBLICATIONS

Xu, Z. et al., "Advances and Impact of Antioxidant Hydrogel in Chronic Wound Healing," Advanced Healthcare Materials, 2020, 9, 1901502. 10.1002/adhm.201901502.

Woodhouse, Ian et al., "Flexible Microneedle Array Patch for Chronic Wound Oxygenation and Biofilm Eradication," ACS Applied Bio Materials, 2021, 4 (7), 5405-5415. doi: 10.1021/acsabm.1c00087.

Cheng et al., "Developing a New Generation of Antimicrobial and Bioactive Dental Resins," Journal of Dental Research, 2017, vol. 96(8): 855-863, doi: 10.177/0022034517709739.

Shcherbakov et al., "CeO2 Nanoparticles-Containing Polymers for Biomedical Applications: A Review," Mar. 17, 2021, Polymers 2021, 3, 924, www.doi.org/10.3390/polym3060924.

OECD Guideline for the Testing of Chemicals No. 439, "In Vitro Skin Irritation: Reconstructed Human Epidermis Test Method," Jul. 23, 2010, OECD Publishing, Paris, https://doi.org/10.1787/9789264090958-en.

Wan, David, (2015). U.N. GHS: United Nations Globally Harmonized System of Classification and Labeling of Chemicals. CIRS. https://www.cirs-group.com/en/chemicals/un-ghs-globally-harmonized-system-of-classification-and-labeling-of-chemicals.

OECD (2021), Test No. 439: In Vitro Skin Irritation: Reconstructed Human Epidermis Test Method, OECD Guidelines for the Testing of Chemicals, Section 4, OECD Publishing, Paris, https://doi.org/10.1787/9789264242845-en.

European Commission Joint Research Centre, "Statement on the Scientific Validity of In-Vitro Tests for Skin Irritation Testing," Institute for Health and Consumer Protection In-vitro Toxicology Unit, European Centre for the Validation of Alternative Methods (ECVAM) Joint Research Centre (ESAC), Nov. 5, 2008.

OECD Guidelines for the Testing of Chemicals, Test Guideline No. 492, "Reconstructed Human Cornea-like Epithelium (RhCE) Test Method for Identifying Chemicals Not Requiring Classification and Labelling for Eye Irritation or Serious Eye Damage," Section 4, Jun. 25, 2018.

Gwak, J.H. et al., "Identifying the trends in wound-healing patents for successful investment strategies," PLoS One, 2017, 12(3): e0174203. https://doi.org/10.1371/journal.pone.0174203.

GHS: Globally Harmonized System of Classification and Labeling of Chemicals (GHS), 8th revised edition, 2019. United Nations—New York and Geneva.

Meng, Z. et al., "Therapeutic Considerations and Conjugated Polymer-Based Photosensitizers for Photodynamic Therapy," Macromolecular Rapid Communications, 2017, 1700614. doi: 10.1002/marc.201700614.

Sadidi, H. et al., "Cerium Oxide Nanoparticles (Nanoceria): Hopes in Soft Tissue Engineering," Molecules. Oct. 6, 2020;25(19):4559. doi: 10.3390/molecules25194559. PMID: 33036163; PMCID: PMC7583868.

Hanafy, B.I. et al., "Cave GWV, Barnett Y, Pierscionek B. Treatment of Human Lens Epithelium with High Levels of Nanoceria Leads to Reactive Oxygen Species Mediated Apoptosis," Molecules. Jan. 21, 2020;25(3):441. doi: 10.3390/molecules25030441. PMID: 31973133; PMCID: PMC7036910.

Bhattacharya, Dipsikha et al., "Accelerated and scarless wound repair by a multicomponent hydrogel through simultaneous activation of multiple pathways," Drug Delivery and Translational Research. Dec. 2019;9(6):1143-1158. doi: 10.1007/s13346-019-00660-z. PMID: 31317345.

Kalaycioğlu, Z. et al., "Antibacterial Nano Cerium Oxide/Chitosan/Cellulose Acetate Composite Films as Potential Wound Dressing," European Polymer Journal (2020), doi: https://doi.org/10.1016/j.eurpolymj.2020.109777.

* cited by examiner

100

200

<u>300</u>

331A    331B

305

330

210

120

<u>400</u>

405

415

420

410

412

500

600

1100

THERAPEUTIC ARTICLE OF MANUFACTURE WITH NANOPARTICLES TO PROMOTE WOUND HEALING AND/OR ANTIMICROBIAL INFECTION CONTROL

CROSS-REFERENCE TO RELATED APPLICATIONS

This application claims priority benefit of U.S. Provisional Application No. 63/272,930, titled "NANOPARTICLES TO PROMOTE WOUND HEALING AND ANTIMICROBIAL INFECTION CONTROL," filed Oct. 28, 2021, incorporated herein by reference in its entirety.

BACKGROUND

Embodiments relate to the field of medical science and, more specifically, the field of medicine for a therapeutic article of manufacture having a barrier to promote wound healing and/or antimicrobial infection control with nanoparticles.

In the United States, approximately 7 million patients struggle with chronic wound healing issues. [See Woodhouse et al., "Flexible Microneedle Array Patch for Chronic Wound Oxygenation and Biofilm Eradication," ACS Appl. Bio Mater. 2021, 4, 5405-5415, Jun. 15, 2021, DOI: 10.1021/acsabm.1c00087.] The chance for infection is high with these types of chronic wounds causing the potential for severe health issues. These wounds easily colonize bacteria either from the person's own skin microbiome, or from other contaminated surfaces, tools or hands.

Wounds that become infected can lead to further serious health complications for the patient, which can be untreatable except through nontraumatic limb amputation. [See Xu et al., "Advances and Impact of Antioxidant Hydrogel in Chronic Wound Healing," Adv. Healthcare Mater. 2020, pgs. 1-11, DOI: 10.1002/adhm.201901502.] Additionally, chronic wound issues often persist due to an inflammation response from the patient's body, not allowing the wound to transition to a proliferative stage where the wound heals and closes. This leaves chronic wound sufferers vulnerable to infection.

SUMMARY

Embodiments relate to wound healing compositions, wound healing articles, wound care articles, and methods of use to treat wounds using a wound healing composite with metal-modified nanoparticles. The embodiments relate to a therapeutic article of manufacture that includes metal-modified nanoparticles in a barrier to eradicate a bacteria and/or a virus trapped in treated fibers of the barrier.

In an aspect, a therapeutic article of manufacture includes a body having fibers treated with a mixture including metal-modified cerium oxide nanoparticles (mCNPs) having a predominant 3+ surface charge and in a range of about 3-35 nanometers (nm) in size, and one or more of a polymeric binder, a dispersant and a stabilizer, the mCNPs are mixed in an amount that is in a range of about 0.01 to 0.1 weight percentage of the mixture and m is an antimicrobial promoting metal that is non-ionizing.

In an aspect, a method is provided that includes applying a barrier using a therapeutic article of manufacture over a portion of an anatomical body part to protect the portion of the anatomical body part; and trapping, by the barrier, at least one of a bacteria and virus to treat the at least one bacteria and virus by the barrier; and eradicating, by the barrier, the at least one of the bacteria and virus.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
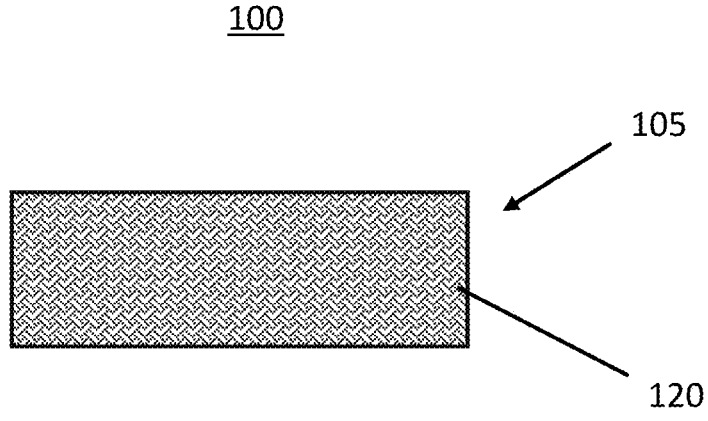
FIG. 1 illustrates a wound care article according to an embodiment.

The inventor has surprisingly determined that metal-modified cerium oxide nanoparticles (mCNPs), as described herein, destroy bacteria and viruses that are found in wounds associated with epithelial tissue layers of the skin or eye and/or subcutaneous tissue. The inventor has determined that the metal-modified nanoceria of about 0.01 to 0.1 weight (wt.) % in a wound healing composite for skin-type wounds is non-toxic and non-irritating.

The inventor has surprisingly determined that metal-modified cerium oxide nanoparticles (mCNPs), as described herein, destroy bacteria and viruses that are found in ocular wounds or epithelial tissue of the eye. The inventor has determined that the metal-modified nanoceria of about 0.01 to 0.1 weight (wt.) % in an ocular wound healing composite for wounds of the eye is non-toxic and non-irritating.

The inventor has surprisingly determined that metal-modified cerium-oxide nanoparticles can retain their synthetic enzyme behavior, using a synthesis technique described herein. These specialized metal bound cerium-oxide nanoparticles can oxidize viruses and bacteria, which cause infections, but also in the presence of a healthy human cell, change its behavior to anti-oxidizing. This behavior allows for antiseptic or antimicrobial properties coupled to inflammation reduction and improved cell growth not common to antimicrobials. In the case of wound healing of the skin or eyes, this allows for faster and more complete wound healing while also preventing infections from a single nanoparticle source.

The metal-modified cerium-oxide nanoparticles, described herein, possess Super Oxide Dismutase (SOD) activity, common to many bio-safe forms of nanoceria. Unlike other nanoceria, the "switch-over" reactions on the nanoceria surface are made fast and more potent by the small presence of discrete silver on the surface of the nanoceria. This allows for quick and facile change in surface behavior of the nanoceria between creation of oxidizing species that are harmful to viruses and bacteria, and to free radical scavenging behavior (antioxidant behavior) that is beneficial to healthy cells. This allows for targeted control of surface reactions from a single material that is able to assist in decrease of inflammation response and support cell growth while also able to target oxidizing behavior directly to viruses and bacteria. This allows for a single system to be an antiseptic to a wound while promoting closure of the wound.

Both wound healing and antimicrobial activity can simultaneously be improved with introduction of ultraviolet (UV) light to the metal mediated cerium oxide nanoparticles. UV light may be introduced via an external light source or with the wound healing apparatus via an up-conversion material that converts visible light to UV or NIR light to UV. [See Meng et al., "Therapeutic Considerations and Conjugated Polymer-Based Photosensitizers for Photodynamic Therapy," Macromol. Rapid Commun. 2017, 1700614, pgs. 1-15, DOI: 10.1002/marc.201700614.] This process may be assisted by polymer conjugation with a photosensitive polymer, such as Tetra-pyrrole structures, or other polymers such as PEG embedded with an up-conversion molecule. This process allows for faster antiviral and antibacterial deactivation in wound healing applications where the wound being treated has its kinetics slowed by oxygen or water diffusion, where the light activation would assist speeding the kinetics of both antiviral and antibacterial activity, as well as free radical scavenging to assist damaged cells in the healing process. Examples of the need for this are for very large or deep wounds, where a light therapy may be applied to speed the recovery process and prevent infection.

The inventor has determined that most bio-safe antimicrobials and antiseptics are oxidizing and not able to switch their response based on the type of cell presented to it. Nanoceria, known as an antioxidant, has had less success as an antimicrobial. This is because the rate of the surface reaction on nanoceria is low compared to the number of species it would need to deactivate in a given time period (i.e., $10^5$ viral load or $10^8$ colony-forming unit (CFU) of bacteria). The mCNPs, described herein, allow for quicker electron recovery of the nanoceria so that it can quickly regenerate its surface creation of oxidizing species. When water is present, this reaction can occur rapidly by digestion of the water by mCNPs, described herein, to these oxidizing species. When a healthy cell is present, the local environment (i.e., potential hydrogen (pH)) switches the behavior of the mCNPs to be free radical scavenging instead.

Definitions

Unless specifically stated or obvious from context, as used herein, the term "about" is understood as within a range of normal tolerance in the art, for example, within 2 standard deviations of the mean. "About" can be understood as within 30%, 25%, 20%, 15%, 10%, 9%, 8%, 7%, 6%, 5%, 4%, 3%, 2%, 1%, 0.5%, 0.1%, 0.05% or 0.01% of the stated value. Unless otherwise clear from context, all numerical values provided herein are modified by the term "about."

As used herein, the term "epithelial tissue" may include any epithelial tissue including, without limitation, skin, corneal epithelium or the like.

As used herein, the term "composition" or "composite" refers to a product that includes ingredients such as one or more of chemical elements, excipient, diluent, binder, tissue glue, tissue adhesive, surgical glue, an epithelial tissue healing agent, skin healing agent, pharmaceutically acceptable carrier, pharmaceutical agent, or constituent in specified amounts, in addition to any product which results, whether directly or indirectly, from a combination of the ingredients in the specified amounts.

The term "pharmaceutically acceptable" component, as used herein, refers to an ingredient that is suitable for use with humans and/or animals without undue adverse side effects (such as toxicity, irritation, and allergic response) commensurate with a reasonable benefit/risk ratio.

A "pharmaceutically acceptable composition" may contain a pharmaceutically acceptable carrier for delivery or administration of the epithelial tissue healing agent or wound healing composition. The pharmaceutical acceptable compositions may be in the form of solid, semi-solid or liquid dosage forms such as, for example, ointments, liquids, lotions, tablets, powders, pills, capsules, suspensions, or suppositories, or preferably in unit dosage form suitable for single administration of a precise dosage. The pharmaceutically acceptable compositions may include an effective amount of a selected ingredient in combination with a pharmaceutically acceptable carrier and, in addition, may include other pharmaceutical agents such as anti-viral agents, adjuvants, diluents, buffers, and the like. The ingredient may be administered in dosage formulations containing non-toxic pharmaceutically acceptable carriers, adjuvants and vehicles.

The term "wound," as used herein, refers to chronic wound, skin tissue wound, eye wound, sunburn, surgical incisions, lacerations, diabetic ulcer or wound, venous ulcer or wound, corneal ulcer or wound, retinopathy ulcer or wound and similar categories of wounds.

The term "prevention" or "preventing" of a disorder, disease, or condition, as used herein, refers to, in a statistical sample, a measurable or observable reduction in the occurrence of the disorder, disease or condition in the treated sample set being treated relative to an untreated control sample set, or delays the onset of one or more symptoms of the disorder, disease or condition relative to the untreated control sample set.

As used herein, the terms "subject," "individual" or "patient" refer to a human, a mammal or an animal.

The term "therapeutically effective amount," as used herein, refers to an amount of active compound or pharmaceutical agent that elicits the biological or medicinal response in a tissue, system, animal or human that is being sought by a researcher, veterinarian, medical doctor or other clinician. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

The term "healing," as referred to herein, refers to a process to repair of a wound.

The term "therapeutic," as referred to herein, refers to treatment or care of a patient or wearer for the purpose of preventing and combating disease and/or preventing or limiting the spread of certain bacteria and/or viruses.

The term "eradicates," as referred to herein, refers to treating a detectable number of infective species of a virus and/or bacteria so that no infective species of the virus and/or bacteria after treatment are detectable.

The term "treating" or "treatment," as used herein, covers the treatment of a disorder, disease or condition described herein, in a subject, and includes: (i) inhibiting development of a disorder, disease or condition; (ii) slowing progression of the disorder, disease or condition; (iii) inhibiting, relieving or slowing progression of one or more symptoms of the disorder, disease or condition; and (iv) assisting with a body's naturally occurring processes heal tissue, such as epithelial tissue, and cause the tissue of a wound to close together.

The term "metal-modified cerium oxide nanoparticles," "metal-modified ceria nanoparticles" or "mCNPs," as used herein, refers to cerium oxide nanoparticles coated with or otherwise bound to an antimicrobial promoting metal such as silver, gold, copper, platinum, nickel, zinc, iron, titanium, ruthenium, vanadium, and the like. The term "mCNPs" includes AgCNP2, as described herein. In an embodiment, the metal-associated cerium oxide nanoparticles comprise a particle size in the range of 3 nm-5 nm or from 1 nm-7 nm.

In some embodiments, the mCNP ingredient with predominately Ce 3+ cerium oxide surface charge may have a particle size in the range of 3 nm-35 nm.

As sometimes used herein, cerium oxide nanoparticles is referred to as "nanoceria."

The inventor has determined that AgCNP1 is catalase mimetic.

The AgCNP1 and AgCNP2 are enzyme mimetic non-stoichiometric nano-cerium oxide. The silver of the synthesis for AgCNP1 and AgCNP2 is a stable metallic silver that is non-ionizing. While not wishing to be bound by theory, the synthesis makes it so that a few atomic layers of the stable metallic silver is anchored into the cerium oxide and contributes to cerium oxide activity (+3 and super oxide dismutase), as opposed to be the direct antimicrobial.

The term "predominant 4+ surface charge" refers to the concentration of cerium ions on the surface and means that the [Ce3+]:[Ce4+] ratio on the surface of the cerium oxide nanoparticle is less than 50%. In a specific example, cerium oxide nanoparticles having a predominant 4+ surface charge have a [Ce3+]:[Ce4+] ratio that is 40% or less. The term "predominant 3+ surface charge" means that the [Ce3+]: [Ce4+] ratio on the surface of the cerium oxide nanoparticle is greater than 50%.

Overview

Diabetes is known to complicate wound healing in many patients and cause ulcers in feet and eyes, for example. Additionally, patients that suffer from circulation issues in their extremities, such as legs, are prone to venous ulcers. These ulcers can become very painful if not treated and lead to more infectious diseases or complications.

Example treatments for wound healing include a wound healing article or wound healing dressings such as antimicrobial dressings, anti-inflammatory dressings, analgesic dressings, combination of anti-inflammatory and analgesic dressings, and advanced dressings containing biological or naturally derived agents, etc. [See Gwak et al. "Identifying the Trends in Wound-Healing Patents for Successful Investment Strategies," PLOS ONE, Mar. 17, 2017, pages 1-19, DOI: 10.1371/journal.pone.0174203, incorporated herein by reference in full.]

Figure 2:
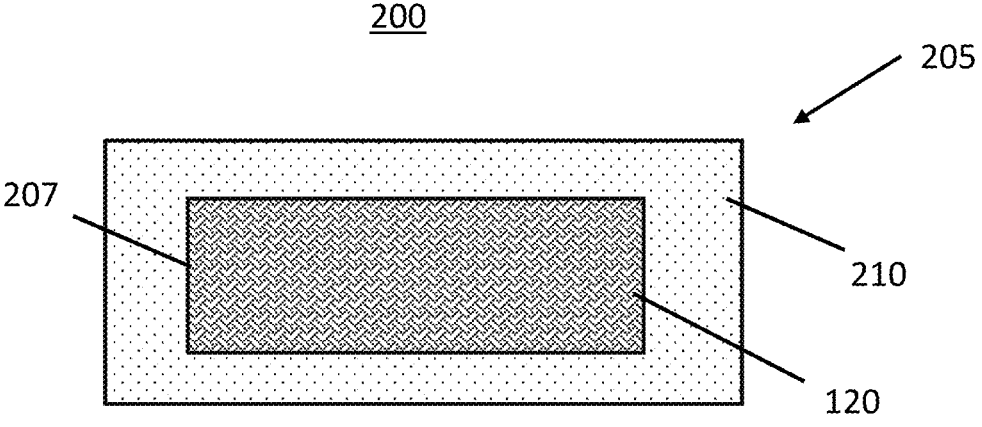
FIG. 2 illustrates a wound care article according to an embodiment.
Figure 3:
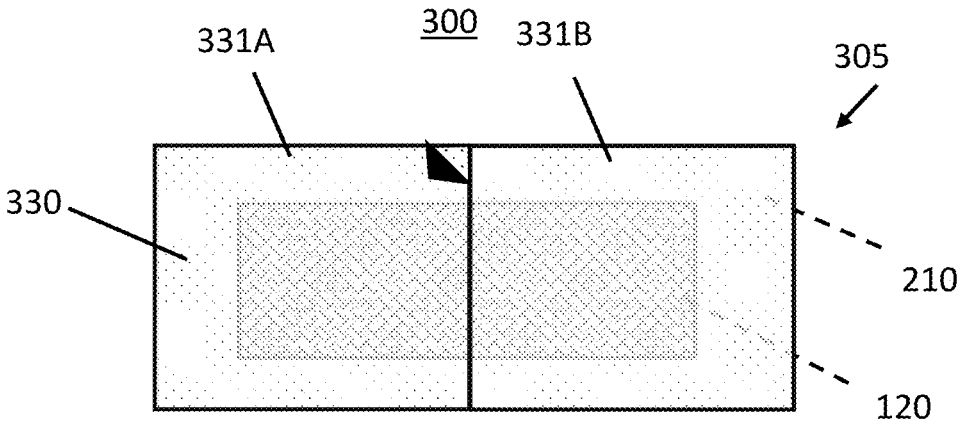
FIG. 3 illustrates a wound care article according to an embodiment.

In some embodiments, treatments for wound healing may include applying a therapeutic dosage of epithelial tissue healing agent to a fiber pad of a wound care article described in relation to FIGS. 1-3 to form a wound healing article including both the wound care article and the therapeutic dosage of the epithelial tissue healing agent; and applying the wound healing article to a wound.

In some embodiments, treatments for wound healing may include applying a wound healing article comprising a fiber pad of a wound care article to a wound.

In some embodiments, treatments for wound healing may include applying a wound healing article that includes a wound care article described in relation to FIGS. 1-3 to a wound healing article to a wound.

In some embodiments, treatments for wound healing may include applying a therapeutic dosage of wound healing composition to a fiber pad of a wound care article, described in relation to FIGS. 1-3 to form a wound healing article including both the wound care article and the therapeutic dosage of the wound healing composition.

In some embodiments, treatments for wound healing may include applying a therapeutic dosage of tissue glue, tissue adhesive, or surgical glue on the wound and covering or dressing a wound or surgical incision with a wound care article, described in relation to FIGS. 1-3.

As described herein, the wound care articles, wound healing articles, and articles incorporating treated fiber material treated with a solution including a mixture of 0.01 wt % of mCNP ingredient and one or more of a binder, a dispersant and a stabilizer, described herein, are a therapeutic article of manufacture. The mCNP ingredient of the therapeutic article of manufacture includes mCNPs that have a predominant 3+ surface charge and are in a range of about 3-35 nanometers (nm) in size and the metal (m) is a stable non-ionizing metal that has antimicrobial promoting properties.

The therapeutic article of manufacture includes treated fibers that eradicate bacteria, such as *Streptococcus mutans* and *Staphylococcus aureus.*

The therapeutic article of manufacture includes treated fibers that eradicate respiratory viruses, such as Rhinovirus 14, SARS-CoV-2 surrogate OC43 coronavirus and Parainfluenza virus type 5.

The therapeutic article of manufacture includes treated fibers that eradicate bacteria, such as *Streptococcus mutans* and *Staphylococcus aureus*, and viruses, such as Rhinovirus 14, SARS-CoV-2 surrogate OC43 coronavirus and Parainfluenza virus type 5.

The therapeutic article of manufacture includes treated fibers in a form factor designed as a barrier which can also treat a wound, incision or laceration formed in the epidermis or other anatomic tissue by preventing formation of bacteria, such as *Streptococcus mutans* and *Staphylococcus aureus.*

The therapeutic article of manufacture includes treated fibers in a form factor designed as a barrier which can protect the wearer from inhaled air from inspiration or inhalation that includes viruses, such as Rhinovirus 14, SARS-CoV-2 surrogate OC43 coronavirus and Parainfluenza virus type 5; and/or expiration particles that may include viruses, such as Rhinovirus 14, SARS-CoV-2 surrogate OC43 coronavirus and Parainfluenza virus type 5, trapped in the treated fibers.

The therapeutic article of manufacture includes treated fibers in a form factor designed as a barrier which can limit the spread of viruses, such as Rhinovirus 14, SARS-CoV-2 surrogate OC43 coronavirus and/or Parainfluenza virus type 5 upon expiration or exhalation of the wearer carrying such virus.

The therapeutic article of manufacture promotes wound healing and/or antimicrobial infection control.

FIG. 1 illustrates a wound care article 100 according to an embodiment. The wound care article 100 may include a body 105 that includes a fiber pad with at least one layer or ply of material, denoted as numeral 120. The material 120 includes sterile fibers. The material fibers may be treated with a solution including a mixture of 0.01 wt % of mCNP ingredient and one or more of a binder, a dispersant and a stabilizer, wherein the mCNP ingredient includes mCNPs that have a predominant 3+ surface charge and are in a range of about 3-35 nanometers (nm) in size and the metal (m) is a stable non-ionizing metal that has antimicrobial promoting properties. The wound care article 100 may be a single-ply gauze material, a gauze pad or a gauze sponge. The gauze pad may have multiple plies of gauze material.

A wound healing article may include a body having fibers treated with a mixture including a polymeric binder with metal-modified cerium oxide nanoparticles (mCNPs). The mCNPs may be further mixed with a dispersant and/or stabilizer to promote adhesion with the binder and/or fibers. In some embodiments, the fibers may be formed of the mixture. The mCNPs have a predominant 3+ surface charge and are in a range of about 3-35 nanometers (nm) in size. The mCNPs are mixed in an amount that is in a range of about 0.01 to 0.1 weight percentage of a mixture having the binder (or binder dispersant and/or stabilizer) and the mCNPs where m is an antimicrobial promoting metal that is non-ionizing.

The polymeric binder may include a biocompatible polymer such as, without limitations, polyethylene glycol (PEG), poly(lactic-co-glycolic acid) (PLGA), PEG-PLGA copolymer, polycaprolactone (PCL), polyethyloxazoline, poly(2-ethyl-2-oxazoline) (EtOx) and polyurethane. The binder may include PetOx which has a CAS No. of 25805-17-8 and a molecular formula of $[C_5H_9NO]n$.

The dispersants and stabilizers may include, without limitation, a cellulose polymer, Bile acids sodium salt, cholic acid-deoxycholic acid sodium salt mixture, Alcohols, C12-14 secondary Ethoxylated Dodecyldimethylamine Oxide (DDAO), Polyethylene Glycol and a block copolymer surfactant. The dispersant and/or stabilizer promote adhesion with the binder and/or the fibers of the body.

The body 105 may include a 4"×4" 8-ply gauze sponge or pad, a 2"×2" 4-ply gauze sponge or pad or a medical grade gauze sponge or pad. For example, the body 105 may include an 8"×10", 12"×12" or 12"×16" gauze sponge or pad for an abdomen for abdominal surgical incisions or lacerations. The body 105 may include any number of layers (i.e., plies) and/or sizes for various parts of the anatomy. For example, the body 105 may include 2-12 plies of cotton fiber material 120. The body 105 may be packaged individually in a sterile packing (not shown). The body 105 may include a length of material that is rolled up or wound to form a bandage roll. The gauze material may be available in a variety of thread counts.

In some embodiments, the term "treated" may include drying or curing a sterile solution with 0.01 wt % of mCNP ingredient, such as AgCNP2 in a range of about 3-35 nanometers (nm) in size, on the fibers of material 120.

In some embodiments, the fiber material 120 may be a blend of material fibers. The fiber material may include one or more of polymers, yarns, cotton and synthetic polymer fibers. In some embodiments, the fiber material 120 may include 100% cotton. The blend of material fibers may include spandex such that the material stretches and/or provides compression to the wound sight when the wound care article is wrapped around a wound. The fiber material 120 may include a moisture-wicking fibers. The fiber material 120 may include a ply of woven fibers and a ply of non-woven fibers. The fiber material 120 may be a non-adhesive material that includes non-adherent fibers that will not stick to a wound.

For example, the material may include a Celox™ gauze material with quick clotting properties.

The wound care article 100 may be a sterile burn dressing. The material may be a gel-soaked medical-grade non-woven material. The wound care article 100 or material 120 may be First Aid Only FAE-3000 series, FAE-5000 series and FAE-7012 compliant. The wound care article 100 may include hydrogel impregnated non-adherent gauze. The hydrogel impregnated non-adherent gauze provides a moist healing environment around the wound wherein the hydrogel (such as, without limitation, PEG or a PEG-PLGA copolymer) is mixed with 0.01 wt % of a mCNP ingredient that has a predominant 3+ surface charge and in a range of about 3-35 nanometers (nm) in size and the metal (m) is a stable non-ionizing metal that has antimicrobial promoting properties.

In some embodiments, the treated fiber material 120 may have a form factor of an ace bandage with elastic fibers. For example, the treated fiber material 120 may be a sterile self-adherent wrap material. Self-adherent wrap material is made by 3M™ Company using a trademark COBAN.

In some embodiments, the treated fiber material 120 compatible with FAE-7012 is used for the treatment of skin burns.

In some embodiments, the treated fiber material 120 treated with a mixture having the mCNP ingredient may have a form factor of STERI-STRIP, such as manufactured by 3M™ Company in Stain Paul, MN, or thin adhesive bandages made by other manufacturers that can be used to close a laceration that may or may not have sutures to hold the skin together.

In some embodiments, the treated fiber material 120 treated with a mixture including the mCNP ingredient may be integrated into an advanced dressings containing biological or naturally derived agents. In some embodiments, the treated fiber material 120 treated with the mCNP ingredient may be integrated into an advanced dressings containing biological or naturally derived agents.

The treated fiber material 120 may have a face mask form factor to prevent or limit spreading a respiratory track illness or lung disease. The treated fiber material 120 may have a face mask form factor for the treatment of a wound to a lung or respiratory track injury from a biological or chemical inhalation or disease. In this case, the fiber material 120 is applied to cover the nostrils of the wearer's nose or mouth. If the wearer exhales a virus, the treated fiber material 120 traps the virus to treat the virus, which eradicates the virus to prevent or limit the spread of the virus. The treated fiber material 120 may also be used to prevent or limit the re-inhalation of the virus by the wearer or inhalation of the virus from the ambient air of the environment.

The treated fiber material 120 may have a replaceable filter form factor configured to be inserted into a face mask or professional breathing protection devices for prevention of wounds or injury to the respiratory track or lungs from Rhinovirus 14, SARS-CoV-2 surrogate OC43 coronavirus and Parainfluenza virus type 5.

The treated fiber material 120 may have N95 Respirator Mask form factor or KN95 Respirator Mask.

The treated fiber material may have a Respirator Mask form factor.

In some embodiments, the treated fiber material 120 treated with a mixture with the mCNP ingredient may be integrated into anti-inflammatory and analgesic dressing.

In some embodiments, the treated fiber material 120 may include impregnated fibers with a wound healing composition described herein.

FIG. 2 illustrates a wound care article 200 according to an embodiment. The wound care article 200 may include a body 205 having a first layer 207 having a pad of fiber material 120 treated with a solution including 0.01 wt % of mCNP ingredient and one of or a combination of polymeric binder, a dispersant and a stabilizer, the mCNPs of the mCNP ingredient has a predominant 3+ surface charge and in a range of about 3-35 nanometers (nm) in size and the metal (m) is a stable non-ionizing metal that has antimicrobial promoting properties. The first layer 207 may include at least one layer or ply of a fiber material (i.e., fiber material 120) or other fibers described above in relation to FIG. 1.

The wound care article 200 may include a second layer 210. The second layer 210 shown hatched with dots. The second layer 210 may be a waterproof layer of material with a coating of low tactile adhesive or glue compatible for adhesion directly onto the surface of skin. The second layer 210 may be a pressure sensitive adhesive layer that adheres to the skin by application of pressure to the low-tactile adhesive. The adhesive layer may be a high-grab/instant tack adhesive. The wound care article 200 may be compatible with International Standardization Organization (ISO) 10993 for medical bandages.

The second layer 210 may be an adhesive strip constructed from thin films (or other types of polymers) such as, without limitations, made from polyurethane or polyethylene, and provide high-grab/instant tack adhesive. The thin films may be such as manufactured by 3M™ Company in Stain Paul, MN.

In some embodiments, the treated fiber material 120 treated with the mCNP ingredient may have a form factor of gauze fibers incorporated into transparent thin films, such as in a 3M™ TAGADERM roll with a transparent film dressing, such as manufactured to 3M™ Company in Stain Paul, MN. An amount of 0.1 wt % of mCNP may be incorporated directly into the adhesive layer of the dressing, in a similar fashion to incorporation into fibers.

In some embodiments, the second layer 210 may include elastic fibers and with a length to surround a portion of the anatomy, such as a wrist, arm, leg, foot, abdomen, chest and head. The elastic fibers may stretch to provide a compressive force around the body with the fiber pad of the first layer overlaying the wound or incision.

The second layer 210 may be affixed to the first layer 207 so that both the first layer 207 and the second layer 210 are applied essentially together to a wound and surrounding skin. Alternately, the second layer 210 may be a separate distinct layer that can be individually applied over the first layer 207 when treating a wound.

FIG. 3 illustrates a wound care article 300 according to an embodiment. The wound care article 300 may include a body 305 having a wound care article 200 with a third layer 330 comprising at least one peel-off liner 331A, 331B. In this example, the wound care article 300 may include two peel-off liners 331A, 331B, which can be peeled away to expose the fiber material 120 and the second layer 210 including an adhesive strip. The third layer 330 may overlay the treated fibers of the fiber pad and the low-tactile adhesive to protect the treated fibers and the low-tactile adhesive until use. The wound care articles 100, 200 and 300 having a treated fiber pad that is treated with an amount of mCNP may be used without a wound healing composition, an epithelial tissue healing agent, tissue glue, tissue adhesive, or surgical glue mixed with an amount of mCNP, described herein. The wound care articles 100, 200 and 300 having a treated fiber pad may be used alone as a wound healing article to protect wounds or incisions from incubation of viruses or bacteria. The wound care articles 100, 200 and 300 may be applied over surgical staples or medical stitches. The wound care articles 100, 200 and 300 may be changed periodically and replaced with new wound care articles as part of a wound care healing treatment regime.

Figure 4:
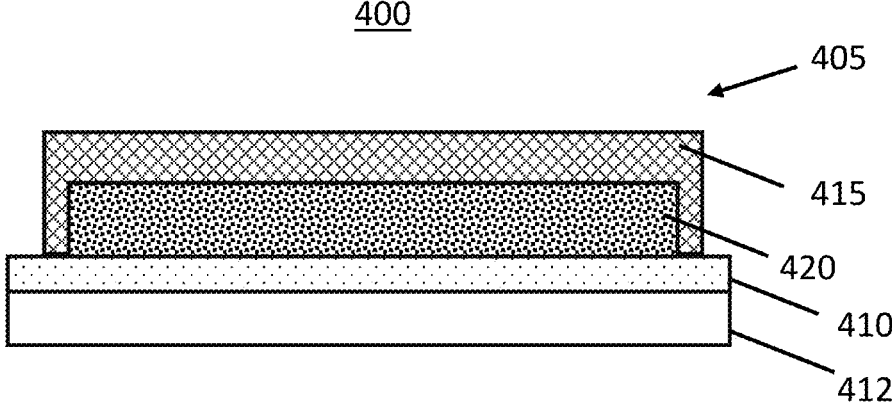
FIG. 4 illustrates a wound healing article according to an embodiment.

FIG. 4 illustrates a wound healing article 400 according to an embodiment. The wound healing article 400 may include a body 405 having a waterproof layer 412 with an adhesive layer 410. The waterproof layer 412 and the adhesive layer 410 may include sublayers that are combined into a single layer. The layer 410 may include a thin-film adhesive that includes a low-tactile adhesive material or high-grab/instant tack adhesive material. In some embodiments, the waterproof layer 412 and adhesive layer 410 may include a self-adherent wrap material. The wound healing article 400 may include, in the body 405, a matrix layer 415 with open pores or a semipermeable membrane which are non-adherent materials. The matrix layer 415 may comprise non-adherent material.

The waterproof layer 412 has a first side that is intended to be exposed when in use. The waterproof layer 412 includes a second side to which the adhesive layer 410 is applied or incorporated.

The wound healing article 400 may include, in the body 405, a pad 420 impregnated with or formed of a mixture or composite that includes an amount of a mCNP ingredient that has a predominant 3+ surface charge and in a range of about 3-35 nanometers (nm) in size and the metal (m) is a stable non-ionizing metal that has antimicrobial promoting properties. For example, the composite may include a mixture of the mCNP ingredient and a therapeutic dosage of epithelial tissue healing agent or wound healing agent. For example, the composite may include a mixture of a hydrogel and the mCNP ingredient which forms a therapeutic dosage of epithelial tissue healing composite. The pad 420 may be surrounded by the matrix layer 415. However, a portion extends beyond the perimeter edges of the waterproof layer 412 and the adhesive layer 410 so that enough surface area is exposed to adhesively bond the wound healing article 400 to the skin of a patient.

Figure 5:
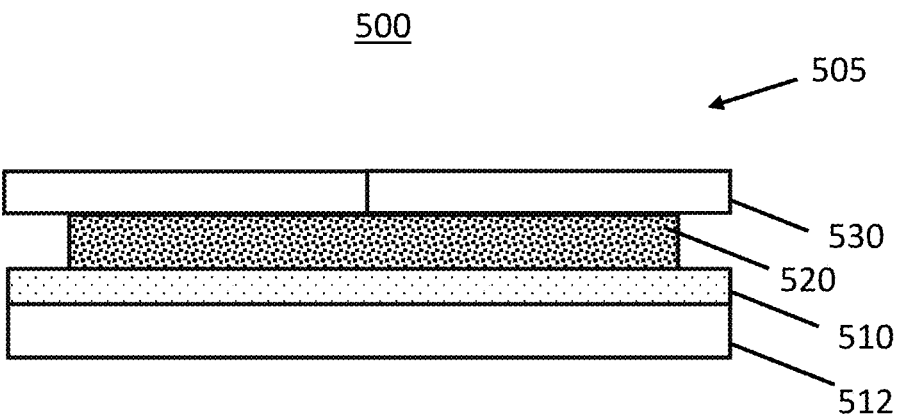
FIG. 5 illustrates a wound healing article according to an embodiment.

Wound healing article 400 may include peel-off liners 530 of FIG. 5.

Wound treatment may include applying the wound healing article 400 to a wound by overlapping a wound or incision with the pad 420 and applying pressure to the waterproof layer 412 and the adhesive layer 410. Additionally, applying slight pressure with a finger to the waterproof layer 412 over the area of the pad 420 causes a therapeutic dosage of epithelial tissue healing composite to pass through the open pores or the semipermeable membrane and onto the wound.

The non-adherent semipermeable membrane or non-adherent porous material of body 5 on top of and surrounding the treated fibers is used to dispense the therapeutic dosage of epithelial tissue healing agent or the wound healing agent through the non-adherent semipermeable membrane or the non-adherent porous material.

FIG. 5 illustrates a wound healing article 500 according to an embodiment. The wound healing article 500 may include a body 505 having a waterproof layer 512 with an adhesive layer 510. The waterproof layer 512 and the adhesive layer 510 may include sublayers that are combined into a single layer. The layer 510 may include a low-tactile adhesive material or high-grab/instant tack adhesive material.

The wound healing article 500 may include, in the body 505, a pad 520 impregnated with or formed of a mixture that includes an amount of mCNPs having a predominant 3+ surface charge and in a range of about 3-35 nanometers (nm) in size and the metal (m) is a stable non-ionizing metal that has antimicrobial promoting properties. The pad may include treated fibers that are impregnated with a healing wound composite. For example, the healing wound composite may include a mixture of the mCNP ingredient and a therapeutic dosage of epithelial tissue healing agent.

The treated fibers may be impregnated fibers impregnated with or formed of a mixture including one or more of a binder, a dispersant and a stabilizer; mCNPs that have a predominant 3+ surface charge and in the range of about 3-35 nanometers (nm) in size; and a therapeutic dosage of epithelial tissue healing agent. The metal (m) is a stable non-ionizing metal that has antimicrobial promoting properties.

The wound healing article 500 may include, in the body 505, at least one liner 530 to cover and protect the pad 520 and or the mixture or composite.

In some embodiments, the bodies 105, 205, 305, 405 and 505 include one of bandages and dressings.

Any of the layers of articles 100, 200, 300, 400 and 500 may be used or substituted in the other articles 200, 300, 400 and 500.

Figure 6:
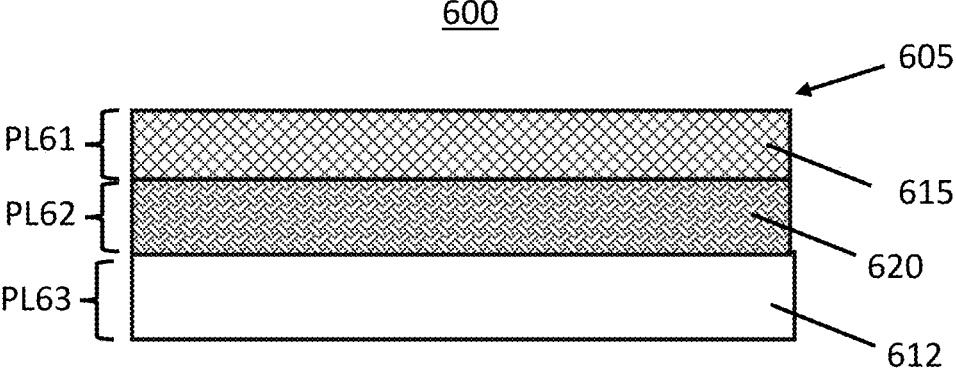
FIG. 6 illustrates a wound healing article having a three-ply structure according to an embodiment.

FIG. 6 illustrates a wound healing article 600 having a body 605 with a three-ply structure according to an embodiment. The body includes a first ply PL61, a second ply PL62 and a third ply PL63. The first ply PL61 may include a first material or fabric 615. In some embodiments, the first material or fabric 415 may be a non-adherent material suitable for dressings or bandages. The second ply PL62 may include treated fiber material 620 (i.e., treated fiber material 120) treated with a mCNP ingredient. The mCNP ingredient includes metal-modified cerium oxide nanoparticles (mCNPs) having a predominant 3+ surface charge and in a range of about 3-35 nanometers (nm) in size. The metal (m) is an antimicrobial promoting metal that is non-ionizing. The treated fiber material 120 may be treated with a mixture including the mCNPs and one or more of a polymeric binder, a dispersant and a stabilizer. The mCNPs are mixed in an amount that is in a range of about 0.01 to 0.1 weight percentage of the mixture.

The third ply PL63 includes a third material or fabric 612. The third material or fabric 612 may be the same material or different as the first material or fabric 615. In some embodiments, the first and third material or fabric 615 and 612 may be untreated gauze or 100% cotton with the second ply PL62 being treated gauze fibers, for example. In other embodiments, the first and third material or fabric 615 may be N95 Respirator Mask materials with an interior embedded layer corresponding to the second ply PL62 with treated fiber material 620 (i.e., fiber material 120).

In some embodiments, a ply may include one or more layers of a fabric or material for a dressing or bandage.

Figure 7:
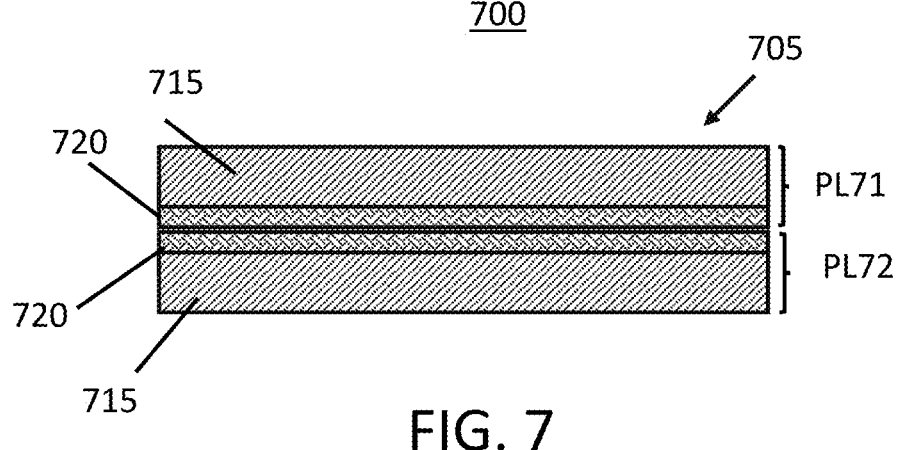
FIG. 7 illustrates a wound healing article having a two-ply structure according to an embodiment.

FIG. 7 illustrates a wound healing article 700 having body 705 with a two-ply structure according to an embodiment. The body 705 includes a first ply PL71 and a second ply PL72. The first ply PL71 may include a first material or fabric 715. The second ply PL72 may include the first material or fabric 715. A portion of the first ply PL71 and the second ply PL72 includes treated fiber material 720 treated with a mCNP ingredient, as described above in relation to FIG. 6. The body 705 includes stacked plies where directly opposing or interior surfaces of the first and second plies PL71 and PL72 are treated fiber material 720 treated with a mixture including the mCNPs and one or more of a polymeric binder, a dispersant and a stabilizer. The mCNPs are mixed in an amount that is in a range of about 0.01 to 0.1 weight percentage of the mixture.

Figure 8:
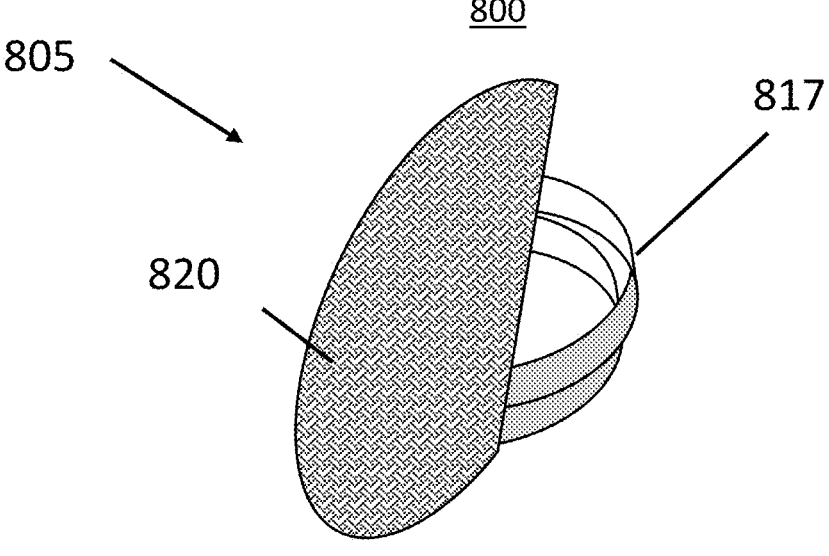
FIG. 8 illustrates a side view of a wound healing article with a face mask form factor according to an embodiment.

FIG. 8 illustrates a side view of a wound healing article 800 with a face mask form factor according to an embodiment. The body 805 of the wound healing article 800 may include at least one ply or layer of treated fiber material 820. The body 805 may include straps 817, one on each side of the body 805, configured to be worn about ears of a wearer. Alternately, the body 805 may include at least one strap 817 having one end attached to a first side of the body and a second end attached to a second end of the body so that the at least one strap 817 may be placed around the back of a head or neck of the wearer. The body 805 may include two-ply structure shown in FIG. 7 or a three-ply structure shown in FIG. 6, for example.

The wound healing articles may be applied to at least one of the mouth and nose or areas adjacent to the breath stream from at least one of the mouth and nose. The wound healing articles described herein may be used to continually reduce the viral load near the mouth and nose and also prevent bacterial growth (from *Streptococcus mutans* and *Staphylococcus aureus*) that people just have around their mouths and nose.

Figure 9:
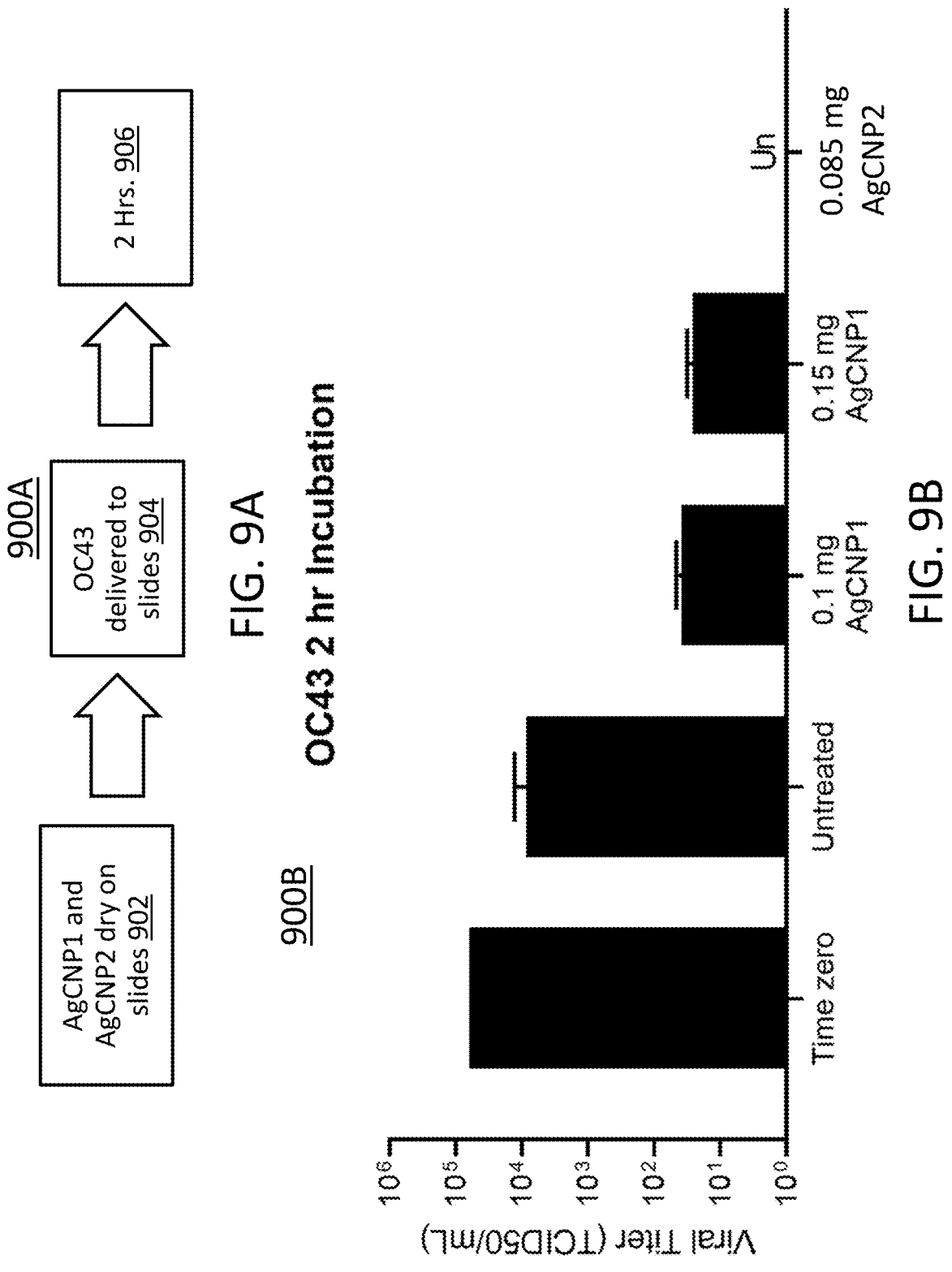
FIG. 9A illustrates a flow diagram of a testing process for viruses such as SARS-CoV-2 surrogate OC43 coronavirus in accordance with an embodiment.
FIG. 9B illustrates a graphical representation of a test of AgCNP1 and AgCNP2 dried on a slide after a 2-hour incubation with SARS-CoV-2 surrogate OC43 coronavirus.

FIG. 9A illustrates a flow diagram of a testing process 900A for viruses, such as SARS-CoV-2 surrogate OC43 coronavirus, in accordance with an embodiment. The process includes, at block 902, drying a solution having a PetOx (binder) compound and a mCNP ingredient of: AgCNP1 in the amount of 0.1 mg on a first slide; AgCNP1 in the amount of 0.15 mg on a second slide; or AgCNP2 in the amount of 0.085 mg on a third slide.

The process may include, at block 904, delivering SARS surrogate OC43 to each of the first, second and third slides. The process may include, at block 906, incubating for 2 hours the slides with the combined SARS-CoV-2 surrogate OC43 coronavirus and mCNP ingredient. The process also delivered SARS-CoV-2 surrogate OC43 coronavirus as a control to an untreated slide.

FIG. 9B illustrates a graphical representation 900B of a test of AgCNP1 and AgCNP2 dried on a slide after a 2-hour incubation with SARS-CoV-2 surrogate OC43 coronavirus.

The untreated slide after 2 hours of incubation had a viral titer of slightly less than $10^4$ mean tissue culture infectious dose (TCID 50/mL). The slide with SARS-CoV-2 surrogate OC43 coronavirus and the solution with the mCNP ingredient of AgCNP1 in the amount of 0.1 mg after 2 hours of incubation have a viral titer of about $1.5 \times 10^2$. The slide with SARS-CoVo2 surrogate OC43 coronavirus and the solution with the mCNP ingredient of AgCNP1 in the amount of 0.15 mg after 2 hours of incubation have a viral titer of about $1.4 \times 10^2$. The slide with SARS-CoV-2 surrogate OC43 coronavirus and the solution of the mCNP ingredient of AgCNP2 in the amount of 0.085 mg after 2 hours of incubation have a viral titer that was undetectable (Un).

The fabrics could be a 2 or 3-ply variation for respiratory viruses (*rhinovirus*, influenza, coronavirus, etc.).

Figure 10:
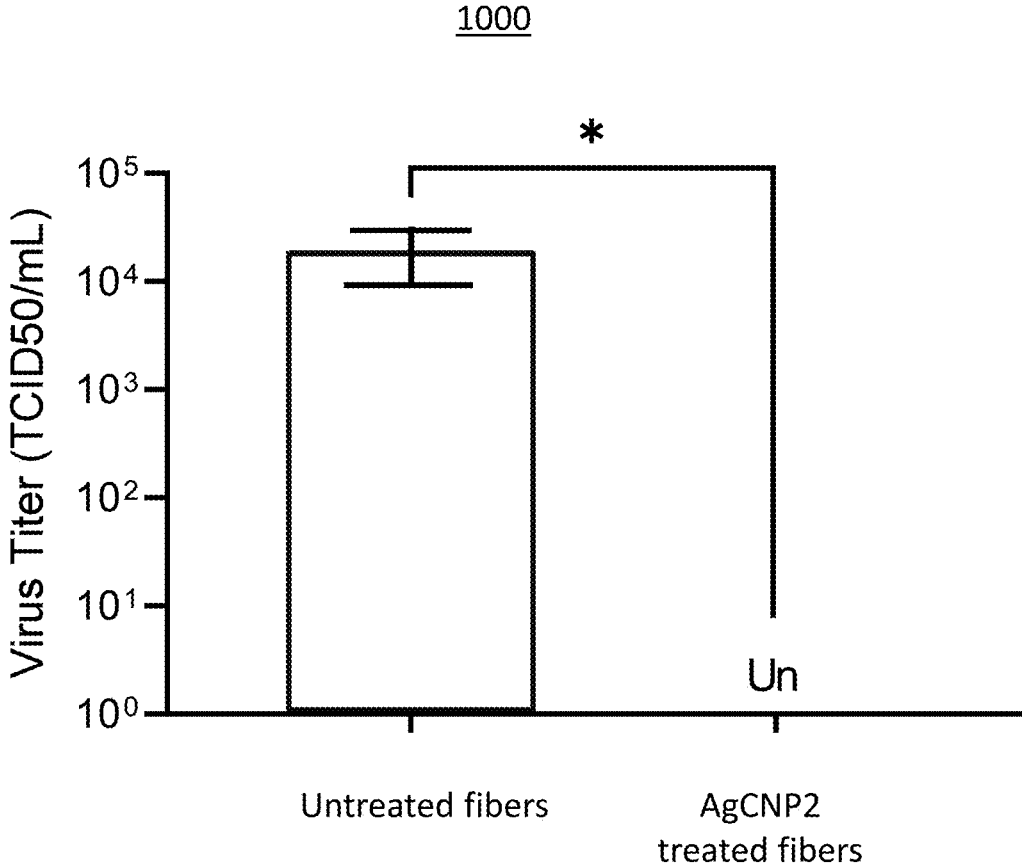
FIG. 10 illustrates a graphical representation of a test that includes fibers treated with a solution including 0.01 wt % of AgCNP2 with a polymeric binder (right) compared to untreated fibers (left) after a 2-hour incubation with Rhinovirus 14 (left and right) on dry fabric.

FIG. 10 illustrates a graphical representation 1000 of a test that includes fibers treated with a polymeric binder that include 0.01 wt % of AgCNP2 (right) compared to untreated fibers (left) after a 2-hour incubation with human Rhinovirus 14 (HRV14) (left and right) on dry fabric. After 2 hours, no infectious (surviving) human Rhinovirus 14 virus (HRV14) was found on the fibers.

Figure 11:
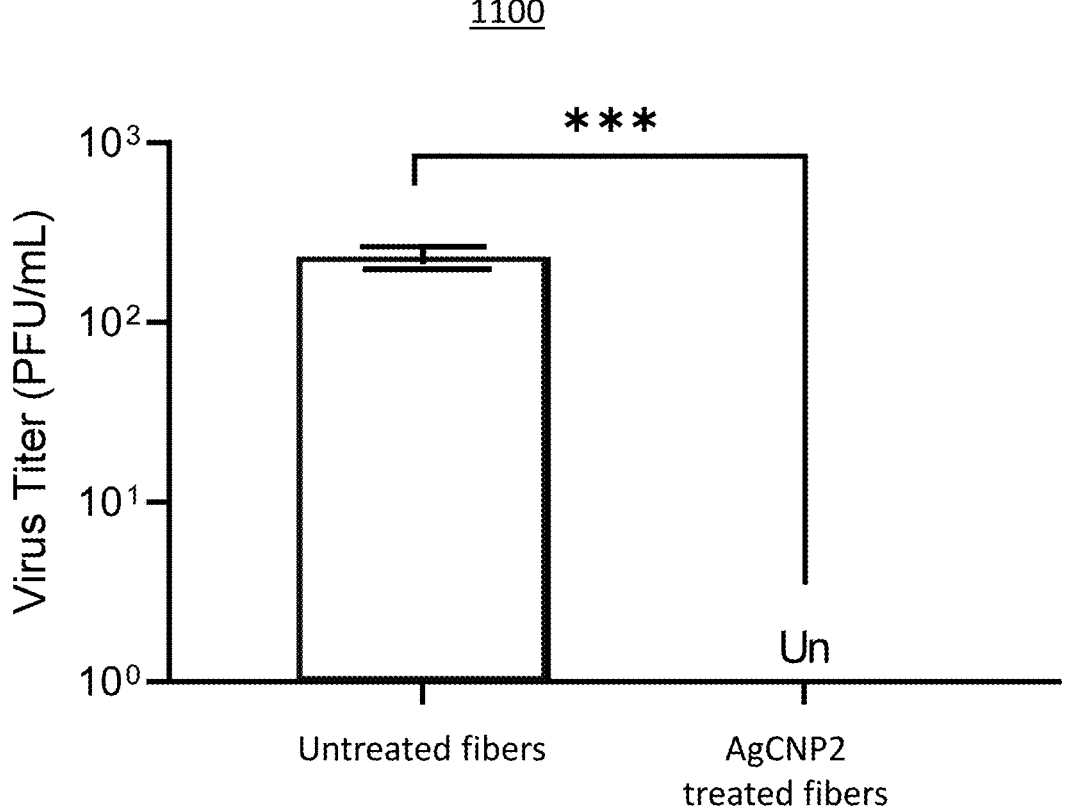
FIG. 11 illustrates a graphical representation of a test that includes fibers treated with a solution including 0.01 wt % AgCNP2 and a polymeric binder (right) compared to untreated fabric (left) after a 2-hour incubation with Parainfluenza virus type 5 (left and right) on dry fibers.

FIG. 11 illustrates a graphical representation 1100 of a test that includes fibers treated with a polymeric binder that includes 0.01 wt % AgCNP2 (right) compared to untreated fabric (left) after a 2-hour incubation with Parainfluenza virus type 5 (PIV5) (left and right) on dry fibers. After 2 hours, no infectious (surviving) Parainfluenza virus type 5 (PIV5) was found on the fibers.

The wound healing article that includes a wound care article 100 may eradicate PIV5 and HRV14. By way of non-limiting example, wound healing article may be worn by a sick person to prevent or limit the spread of HRV14.

Metal-Modified Cerium Oxide Nanoparticle (AgCNP2)

Using a forced hydrolysis reaction, a solution containing silver-modified nanoceria and silver secondary phases were formed, hereinafter referred to as "material." The material was washed with distilled water. Then, the washed material was treated with ammonium hydroxide ($NH_4OH$). The material was also treated with a phase transfer complex: mediating aqueous dispersion of dissolved silver, (Ag $[(NH_3)_2OH]_{aq}$). After treatment, the treated material was washed again such as by distilled water. In another synthesis that yields silver modified nanoceria, silver nitrate ($AgNO_3$) and cerium (Ce) are dissolved to form a mixture. Then the mixture is dissolved by hydrogen peroxide ($H_2O_2$) which causes selective oxidation of $Ce^{3+}$ over silver and the evolution of metallic silver phases on the ceria surface. The formula properties for AgCNP2 is shown below in Table 1.

TABLE 1

|  | AgCNP2 | Inorganic Crystal Structure Database No. (ICSD #) |
|---|---|---|
| $Ce^{3+}:Ce^{4+}$ (% $Ce^{3+}$)(%) | 53.7 |  |
| [Ag]/Ag + Ce] by XPS(%) | 4.6 |  |
| SOD Activity (% Inhibition) | 99.2 |  |
| Hydrodynamic Diameter (nm) | 31.6 ± 2.4 |  |
| Zeta Potential (mV) | 24.1 ± 1.3 |  |
| ICPMS Ce concentration (ppb) | 299.2 ± 1.3 |  |
| $E_{corr}$ (mV) | 217.374 |  |
| Metallic Ag |  | 44387 |
| $CeO_2$ |  | 55284 |

A process for metal-mediated nanoscale cerium oxide is described in Craig J. Neal et al., titled "schemMetal-Mediated Nanoscale Cerium Oxide Inactivates Human Coronavirus and Rhinovirus by Surface Disruption," ACS Publications, ACSJCA 8/23/2021, doi.org/10.1021/acsnano.1c04142, incorporated herein by reference in its entirety.

A Zeta-sizer nano was used from Malvern Instruments to determine hydrodynamic diameters and zeta potentials. Tafel analysis for AgCNP2 shows distinct corrosion potentials. $E_{corr}$ values are substantially more noble than pure silver.

A more detailed description of the process for forming AgCNP2 will now be described. First, about 109 mg of cerium nitrate hexa-hydrate (99.999% purity) is dissolved in about 47.75 mL $dH_2O$ in a 50 ml square glass bottom. Then, about 250 μL of 0.2 M aq. $AgNO_3$ (99% purity) is added to the cerium solution above with the solution vortexed for 2 minutes: Machine: Vortexer. Then, about 2 mL of 3% hydrogen peroxide (stock) is added quickly to the above solution followed by immediate vortexing for 2 minutes at highest rotation speed (in vortexer machine). This solution is stored in dark condition at room temperature with the bottle (50 mL square bottom glass) cap loose to allow for release of evolved gases; solutions are left to age in these conditions for up to 3 weeks (monitoring solution color change from yellow to clear) to create 50 ml total volume of the solution. Particles are then dialyzed against 2 liters of dH2O over 2 days, (dialysis Tubing) with the water changed every 2 hours and stored in the same conditions as for ageing.

The two unique formulations of cerium oxide nanoparticles are produced with surfaces modified by silver nanophases. Materials characterization shows that the silver components in each formulation are unique from each other and decorate the ceria surface as many small nanocrystals (AgCNP1) or as a Janus-type two-phase construct (AgCNP2). The average diameter of AgCNP1 is about 20 to 24 nm, and the average diameter of AgCNP2 is about 3 to 5 nm. However, the inventor prefers the use of AgCNP2, for the reasons stated below.

Each synthesis further possesses unique mixed valency with AgCNP2 possessing a significantly greater fraction of $Ce^{3+}$ states relative to $Ce^{4+}$ over AgCNP1. The distinct valence characters, along with incorporation of chemically active silver phases, lead to high catalytic activities for each formulation. AgCNP2 possesses high superoxide dismutase activity, while AgCNP1 possesses both catalase and superoxide dismutase-like enzyme-mimetic activities, ascribed to the catalase activity of ceria and the superoxide dismutase activity from silver phases.

Further, analysis demonstrates that silver incorporated in each formulation is substantially more stable to redox-mediated degradation than pure silver phases: promoting an increased lifetime in catalytic applications and low probability of ionization of the silver phase.

Although the amount is not intended to be limiting, when used in methods of the invention, some preferred amounts of silver percentages associated with the AgCNPs are about 8% to 15% or less.

In other embodiments, disclosed is a method of producing mCNPs, as described herein, may include the metal of silver. Further the AgCNP2 is produced via a method comprising dissolving cerium and silver precursor salts such as cerium and silver nitrates; oxidizing the dissolved cerium and silver precursor salts via admixture with peroxide; and precipitating nanoparticles by subjecting the admixture with ammonium hydroxide.

Alternatively, the AgCNPs are produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver.

Applications

The wound healing composition for the epithelial tissue including skin or eye tissue to target the oxidizing response need to kill viruses and bacteria to the virus and bacteria. Additionally, wound healing composition may include an epithelial tissue healing agent and AgCNP2, which acts as an antioxidant in the presence of healthy cells, promoting lower inflammation and cell growth. This allows for quicker closure of the wound while assuring that any trapped bacteria will not lead to an infection. The nature of the wound healing composition is that it works against a broad range of viruses and bacteria.

The epithelial tissue healing agent may be selected from a group consisting of preadipocyte modulator and an adipocyte modulator and contain in a pharmaceutically acceptable composition for subcutaneous administration, as described in U.S. Pat. No. 7,638,484, incorporated herein by reference in its entirety.

The epithelial tissue healing agent may include a therapeutically effective amount of a viral vector comprising a polynucleotide coding for an adipokine, as described in U.S. Pat. No. 7,638,484.

The skin cells colonizing the damaged skin or skin wound may be of any cell type which is involved in the wound healing process, such as keratinocytes, fibroblasts, adipocytes or preadipocytes. The cells can be transformed by a polynucleotide encoding an adipokine as defined hereinbefore. Alternatively, the cells can be transformed by a polynucleotide encoding a polypeptide capable of an adipokine activity, such as the polynucleotide encoding adipsin/complement D activity described in U.S. Pat. No. 5,223,425, incorporated by reference.

The suitable polynucleotide can be introduced into cells by any one of a variety of known methods within the art. Such methods are generally described in Sambrook et al., (1989, 1992), Ausubel et al., (1989), Chang et al., (1995), Vega et al., (1995), Rodriguez and Denhardt (1988) and Gilboa et al., (1986), and include, for example, stable or transient transfection, lipofection, electroporation and infection with recombinant viral vectors. U.S. Pat. No. 4,866,042 discloses a list of vectors involving the central nervous system, and U.S. Pat. Nos. 5,464,764 and 5,487,992 describe positive-negative selection methods for inducing homologous recombination, all of which patents are incorporated herein by reference.

The wound healing composition may include a tissue adhesive or glue and metal-modified cerium oxide nanoparticles (mCNPs) in a range of about 3-5 nm in size and mixed in an amount that is in a range of about 0.01 to 0.1 weight percentage of a mixture having the tissue adhesive and the mCNPs.

The tissue adhesive or glue formulation may include the components for delivery and administration to a surgical incision or wound.

In certain embodiments, the tissue glue may include a fibrin glue. Fibrin glue as a surgical adhesive is well known in the art. The tissue glue may include hydrogels comprising, for example, but not limited to, polyethylene glycol (PEG), fibrin, dextrans, including dextrans suitable for chemical crosslinking and/or photo-crosslinking, albumin, polyacrylamide, polyglycolic acid (PGA), polyvinyl chloride, polyvinyl alcohol, poly(n-vinyl-2-pyrollidone), poly(2-hydroxy ethyl methacrylate), hydrophilic polyurethanes, acrylic derivatives, pluronics, such as polypropylene oxide and polyethylene oxide copolymer (POC), or the like.

The use of fibrin glue as a skin adhesive for closing surgical incisions is well known in the art. The glue compositions may also include additional components such as liposomes, for example. Example fibrin glue compositions are disclosed in U.S. Pat. No. 5,290,552, which is incorporated by reference.

In certain embodiments, the adhesive or glue may comprise non-degradable materials, for example, but not limited to, expanded polytetrafluoroethylene (ePTFE), polytetrafluoroethylene (PTFE), polyethyleneterephthalate (PET), polyurethane, polyethylene, polycabonate, polystyrene, silicone, and the like, or selectively degradable materials, such as poly (lactic-co-glycolic acid; PLGA), polylactic acid (PLA) or PGA.

In certain embodiments, the surgical glue or adhesive may be a photo-activated glue, acrylate-based adhesives, and the like.

Example synthetic hydrogels may include polyphosphazenes, poly (vinyl alcohol) (PVA), and an interpenetrating and semi-interpenetrating hydrogels (e.g., PEO, and PEO-PEO-dimethylacrylate blends).

Example tissue adhesives may be a single component adhesive or multi-component adhesive. Further suitable adhesives include synthetic adhesives and/or natural adhesives. Suitable biocompatible adhesives for use in the wound healing composition include commercially available surgical adhesives, such as cyanoacralate (such as 2-octyl cyanoacrylate, Dermabond™) and fibrin glue (such as Tissucol®).

There are many tissue glues, surgical glues, or tissue adhesives readily available on the market. The healing wound composition is applied in a therapeutically effective amount to the wound to close the wound. The amount of AgCNP2 is mixed or dissolved in the wound healing composition in an amount that is a therapeutically effective amount with a surgical adhesive or glue.

The wound healing composition may include a solid composition or a liquid composition, by way of non-limiting example. For a solid composition of a pharmaceutically acceptable composition, conventional nontoxic solid carriers include, for example, pharmaceutical grades of mannitol, starch, magnesium stearate, talc, lactose, glucose, sucrose, sodium saccharin, magnesium carbonate, cellulose, and the like. For liquid pharmaceutically acceptable compositions, the pharmaceutically acceptable composition may be prepared by dissolving, dispersing, mixing, etc., an active compound as described herein and optional pharmaceutical adjuvants in an excipient such as, for example, saline, water, aqueous dextrose, ethanol, glycerol, and the like, to thereby form a solution or suspension. The pharmaceutical acceptable composition may contain minor amounts of nontoxic auxiliary substances such as wetting or emulsifying agents, pH buffering agents and the like, for example, sorbitan mono-laurate, sodium acetate, triethanolamine oleate, triethanolamine acetate, etc. Specifically, the wound healing composition includes an amount of AgCNP2 mixed or dissolved in the wound healing composition includes about 0.01 to 0.1 weight percentage (wt %).

Methods of preparing dosage forms of the pharmaceutical acceptable composition are known, or will be apparent, to those skilled in this art. For oral administration, the pharmaceutical acceptable composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspension is used, the active agent may be combined with emulsifying and suspending agents. If desired, flavoring, coloring and/or sweetening agents may be added as well. Other optional components for incorporation into an oral formulation of the pharmaceutical acceptable composition herein include, but are not limited to, preservatives, suspending agents, thickening agents, and the like. One skilled in this art may further formulate the pharmaceutical acceptable composition in an appropriate manner, and in accordance with accepted practices, such as those disclosed in Remington's Pharmaceutical Sciences, Gennaro, Ed., Mack Publishing Co., Easton, Pa. 1990.

In some embodiments, multiple applications of a wound healing composition may be needed.

Two tests were performed by MB Research Laboratories, in Spinnerstown, PA, using the AgCNP2 described herein. The tests include a skin irritation test (SIT) and an eye irritation test (EIT).

Skin Irritation Test (SIT) and Results

MatTek EpiDerm™ tissue samples were treated with the test articles, negative control, and positive control in triplicate for 60 minutes. Following treatment and subsequent incubation time, the viability of the tissues was determined using thiazolyl blue tetrazolium bromide (MTT) uptake and reduction. The absorbance of each sample was measured at 570 nm. The viability was then expressed as a percent of control values. If the mean tissue viability was 50% or less, the test material was classified as an irritant; if the mean tissue viability was more than 50%, the test material was classified as a non-irritant. The test used MB Protocol Number: 713-03.

Table 2 below identifies the test and control articles, the mean tissue viability percentage (%), the irritancy classification and the GHS classification. The purpose of this study was to provide classification of the dermal irritation potential of chemicals by using a three-dimensional human epidermis model, according to the OECD Guideline for the Testing of Chemicals No. 439, "In Vitro Skin Irritation: Reconstructed Human Epidermis Test Method". [OECD: Organisation for Economic Co-Operation and Development.] The EpiDerm™ SIT allows discrimination between irritants (Category 2) and non-irritants, in accordance with U.N. GHS classification. [U.N. GHS: United Nations Globally Harmonized System of Classification and Labelling of Chemicals.]

TABLE 2

| Test and Control Article Identity | Mean Tissue Viability (%) | Irritancy Classification | GHS Classification |
|---|---|---|---|
| 0.073 wt % AgCNP2 in water | 112.4 | Non-irritant | No Category |
| 0.01 wt % AgCNP2 in water | 105.8 | Non-irritant | No Category |
| Dulbecco's Phosphate-buffered saline (dPBS) (Negative Control) | 100.0 | Non-irritant | No Category |
| 5% Sodium dodecyl sulfate (Positive Control) | 3.1 | Irritant | Category 2 |

Table 3 shows a table of positive controls.

TABLE 3

| Positive Control | |
|---|---|
| Identity | 5% Sodium dodecyl sulfate (SDS), Lot No. 111120BBB |
| Test Article Characterization | |
| Description | Clear colorless liquid |
| Sample Preparation | Used as received |

Table 4 shows a table of negative controls.

TABLE 4

| Negative Control | |
|---|---|
| Identity | Dulbecco's Phosphate-buffered saline (dPBS) Lot No. 2306404 |
| Test Article Characterization | |
| Description | Clear colorless liquid |
| Sample Preparation | Used as received |

Plate Reader Linearity Check

The linearity of the plate reader used for optical density (OD) determination was verified prior to its use the same week the SIT assay was performed. A dilution series of trypan blue was prepared and two 200-μl aliquots per concentration were pipetted into a 96-well plate. The optical density of the plate wells was measured at a wavelength of 570 nm (OD570), with no reference wavelength. A regression line and an R-squared value were generated using Microsoft Excel® 2007. Verification was considered acceptable if the R-squared value was greater than or equal to 0.999.

Test Article Reduction of MTT

For each test article, a total of 50 μl of the test article were mixed with 1 ml of MTT solution (1 mg/ml methyl thiazole tetrazolium diluted in Dulbecco's Modified Eagle's Medium [DMEM]). A negative control (50 μl of tissue culture water, TCH2O) was tested concurrently. The solutions were incubated in the dark at $37\pm1°$ C., $5\pm1\%$ CO2 for approximately 3 hours in a six-well plate. After incubation, the solutions were visually inspected for purple coloration, which indicates that the test article reduced MTT. Since tissue viability is based on MTT reduction, direct reduction by a test article can exaggerate viability, making a test article seem less irritating than its actual irritation potential. None of the test articles were found to have reduced MTT and the assay continued as per the protocol.

Mesh Compatibility

For each test article, pre-cut nylon mesh supplied with the tissues was placed on a slide and 30 μl of the undiluted test article or tissue culture water (negative control) were applied. After 60 minutes of exposure, the mesh was checked microscopically. No interaction between any test articles or tissue culture water and the mesh was observed so the test articles were dosed using the mesh as a spreading aid.

Assessment of Coloring or Staining Materials

The test articles were non-colored; therefore, it was assessed to determine if the extractant would become colored when mixed with the test article. For each test article, a total of 50 μl of the test article were incubated in a six-well plate with 1 ml of TCH2O for at least 1 hour in a humidified $37\pm1°$ C., $5\pm1\%$ CO2 incubator. An additional 50 μl of the test article were added to 2 ml of extractant (isopropanol) and incubated for 2 to 3 hours in a six-well plate, at room temperature with shaking. Two 200 μl aliquots of the test article plus TCH2O or test article plus extractant from each well were transferred to a 96-well plate and measured at 570 nm using a plate reader (μQuant Plate Reader, Bio-Tek Instruments, Winooski, VT). No color developed in the water or the extractant, resulting in an OD570 no more than 0.08 after subtraction of blank (TCH2O or isopropanol, respectively), so no colorant controls were added to the assay.

EpiDerm™ Tissue Samples

EpiDerm™ tissues, Lot No. 35611, Kit F, were received from MatTek Corporation (Ashland, MA) on Jul. 7, 2021, and refrigerated at 2 to 8° C. Before use, the tissues were incubated ($37\pm1°$ C., $5\pm1\%$ CO2) with assay medium (Mat- Tek) for a 1-hour equilibration. The tissues were then moved to new wells with fresh medium for an additional overnight equilibrium, for 18±3 hours. Equilibration medium was replaced with fresh medium before dosing.

Dosing

Each treatment with the test articles or controls was conducted in triplicate. For each test article, 30 μl of the test article were applied to each EpiDerm™ tissue. A nylon mesh was then placed on top to facilitate even distribution of the test article.

A negative control (30 μl of Dulbecco's Phosphate-buffered saline) and a positive control (30 μl of 5% SDS solution) were each tested concurrently, with a nylon mesh placed on top to facilitate even distribution of the material. The exposure period for the test articles and controls was 60 minutes. The dosed tissues were placed in an incubator at 37±1° C., 5±1% $CO_2$ for 35±1 minute, and then returned to the sterile hood for the remainder of the 60-minute exposure period.

After dosing and incubation, the tissues were rinsed with DPBS, blotted to remove the test substance and dry the tissue, and transferred to fresh medium. The rinsed Epi-Derm™ tissues were returned to the incubator for 24±2 hours. Medium was changed at 24±2 hours. Tissues were returned to the incubator for an additional 18±2 hours.

Tissue Viability (MTT Reduction)

Each EpiDerm™ tissue was transferred to a 24-well plate containing 300 μl of MTT solution (1 mg/ml MTT in DMEM). The tissues were then returned to the incubator for an MTT incubation period of 3 hours±10 minutes. Following the MTT incubation period, each EpiDerm™ tissue was rinsed with DPBS and then treated with 2.0 ml of extractant solution (isopropanol) per well for at least two hours, with shaking, at room temperature. Two 200-μl aliquots of the extracted MTT formazan were transferred to a 96-well plate and measured at 570 nm using a plate reader (μQuant Plate Reader, Bio-Tek Instruments, Winooski, VT).

Quality Controls

The assay met the acceptance criteria if the mean OD570 of the negative control tissues was between and 2.8, inclusive, and the mean viability of positive control tissues, expressed as percentage of the negative control tissues, was less than or equal to 20%. In addition, the difference calculated from individual percent tissue viabilities of the three identically-treated replicates was acceptable if it was less than 18%.

Skin Irritation Prediction

According to the EU and GHS classification, an irritant is predicted if the mean relative tissue viability of three individual tissues exposed to the test substance is 50% or less of the mean viability of the negative controls. [EU: OECD Guideline for the Testing of Chemicals No. 439: In Vitro Skin Irritation: Reconstructed Human Epidermis Test Method; and European Centre for the Validation of Alternative Methods (ECVAM) Joint Research Centre (ESAC), Statement on the Scientific Validity of In-Vitro Tests for Skin Irritation Testing.] [GHS: Globally Harmonized System of Classification and Labeling of Chemicals (GHS), 8th revised edition, 2019. United Nations—New York and Geneva.]

Table 5 identifies the irritancy classification and GHS category.

TABLE 5

| In Vitro Result | In Vivo Prediction | |
| --- | --- | --- |
| | Irritancy Classification | GHS |
| Mean tissue viability ≤50% | Irritant | Category 2 |
| Mean tissue viability >50% | Non-Irritant | No Category |

Each tissue in this group had individual relative viabilities greater than 50%, making each tissue non-irritating.

Table 6A is part 1 of a live tissue data table. The table identifies the tissue number to raw data test sample Aliq. 1, Aliq. 2, Aliquots, and mean blank. Table 6B is part 2 of the live tissue data table of Table 5 and identifies the corrected data, mean of Aliquots, OD means and differential, and viabilities both mean and standard deviation.

TABLE 6A

| Test and Control | Tissue | Raw data | | Mean |
| --- | --- | --- | --- | --- |
| Article Identity | No. | Aliq. 1 | Aliq. 2 | Blank |
| 0.073 wt % AgCNP2 in water | 1 | 1.870 | 2.307 | 0.047 |
| | 2 | 2.189 | 2.154 | |
| | 3 | 1.722 | 1.698 | |
| 0.01 wt % AgCNP2 in water | 1 | 1.857 | 2.108 | 0.047 |
| | 2 | 1.867 | 1.826 | |
| | 3 | 1.789 | 1.806 | |
| Dulbecco's Phosphate-buffered saline (dPBS) (Negative Control) | 1 | 1.861 | 1.752 | 0.047 |
| | 2 | 1.600 | 1.652 | |
| | 3 | 1.939 | 1.850 | |
| 5% Sodium dodecyl sulfate (SDS) (Positive Control) | 1 | 0.091 | 0.112 | 0.047 |

TABLE 6B

| Test and Control | Tissue | Corrected Data | | Mean of | % | OD | | Viabilities (%) | |
| --- | --- | --- | --- | --- | --- | --- | --- | --- | --- |
| Article Identity | No. | Aliq. 1 | Aliq. 2 | Aliquots | Viability | Mean | Diff. | Mean | SD |
| 0.073 wt % AgCNP2 in water | 1 | 1.823 | 2.260 | 2.042 | 118.1 | 1.943 | 0.246 | 112.4 | 14.2 |
| | 2 | 2.142 | 2.107 | 2.125 | 122.9 | | | | |
| | 3 | 1.675 | 1.651 | 1.663 | 96.2 | | | | |
| 0.01 wt % AgCNP2 in water | 1 | 1.810 | 2.061 | 1.936 | 112.0 | 1.829 | 0.096 | 105.8 | 5.5 |
| | 2 | 1.820 | 1.779 | 1.800 | 104.1 | | | | |
| | 3 | 1.742 | 1.759 | 1.751 | 101.3 | | | | |
| Dulbecco's Phosphate-buffered saline (dPBS) (Negative Control) | 1 | 1.814 | 1.705 | 1.760 | 101.8 | 1.729 | 0.137 | 100.0 | 7.9 |
| | 2 | 1.553 | 1.605 | 1.579 | 91.3 | | | | |
| | 3 | 1.892 | 1.803 | 1.848 | 106.9 | | | | |
| 5% Sodium dodecyl sulfate (SDS) (Positive Control) | 1 | 0.044 | 0.065 | 0.055 | 3.2 | 0.054 | 0.003 | 3.1 | 0.1 |
| | 2 | 0.052 | 0.050 | 0.051 | 3.0 | | | | |
| | 3 | 0.059 | 0.053 | 0.056 | 3.2 | | | | |

Table 7 identifies the OD blank values.

TABLE 7

| Tissue: | 1 | 2 | 3 | 4 | 5 | 6 | Mean Blank OD |
|---------|-----|-----|-----|-----|-----|-----|---------------|
| OD: | 0.048 | 0.046 | 0.046 | 0.048 | 0.047 | 0.046 | 0.047 |

Quality Controls

The mean OD570 of the negative control tissues was 1.729, which met the acceptance criteria of greater than or equal to 0.8 and less than or equal to 2.8. The mean relative viability of the positive control tissues was 3.1%, which met the acceptance criterion of less than or equal to 20%. The standard deviation in viability between identically treated tissues were 0.1% to 19.6%, which did not meet the acceptance criterion of less than 18%. The R-squared value calculated for the plate reader linearity check was 0.9997, which met the acceptance criterion of greater than or equal to 0.999.

Table 8 identifies the PBS. Dulbeccos W/O CA. MG (1×) with an origin of the UK.

TABLE 8

| Test | Specification | Result | Units |
|------|---------------|--------|-------|
| a01 Bacterial | Negative | Negative | |
| a02 Fungal | Negative | Negative | |
| a96 Endotoxin | 0.000 to 0.500 | 0.040 | EU/mL |
| b01 Ph | 7.00 to 7.30 | 7.17 | pH Units |
| b02 Osmolality | 270 to 300 | 283 | mOs/kg H2O |
| b33 Volume | Satisfactory | Satisfactory | |
| q01 Documentation | Satisfactory | Satisfactory | |
| q02 Appearance (Liquid) | Satisfactory | Satisfactory | |

Sterile filtered (0.1 µm); Sterility testing (Test Numbers a01, a02) is carried out in accordance with *Ph. Eur. 2.6.1* and *USP 7.1*

Eye Irritation Test (EIT) and Results

MatTek EpiOcular™ tissues were treated with the test articles, negative control and positive control in duplicate for 30 minutes. Following treatment and subsequent incubation time, the viability of the tissues was determined using thiazolyl blue tetrazolium bromide (MTT) uptake and reduction. The absorbance of each sample was measured at 570 nm. The viability was then expressed as a percent of negative control values. If the mean tissue viability were less than or equal to 60%, the test material was classified as an Irritant (UN GHS Category 1 or 2); if the mean tissue viability were greater than 60%, the test material was classified as UN GHS No Category, and was therefore interpreted to be Non-irritant. The MB protocol: 772.

Table 9 shows the irritancy classification and GHS classification, as well as the tissue viability for mean and difference for each test article.

The summarized results and irritation classifications are as follows, as shown in Table 9:

TABLE 9

| Test and Control Article Identity | Tissue Viability (%) Mean | Diff. | Irritancy Classification | GHS Classification |
|-----------------------------------|------|------|--------------------------|---------------------|
| Test Article 1: 0.073 wt % AgCNP2 in water | 96.8 | 13.47 | Non-Irritant | No Category |
| Test Article 2: 0.01 wt % AgCNP2 in water | 105.2 | 4.61 | Non-Irritant | No Category |
| Tissue Culture Water (Run 1) (Negative Control) | 100.0 | 2.51 | Non-Irritant | No Category |
| Methyl acetate (Run 1) (Positive Control) | 30.1 | 4.28 | Irritant | Category 1 or 2 |

TABLE 9-continued

| Test and Control Article Identity | Tissue Viability (%) Mean | Diff. | Irritancy Classification | GHS Classification |
|-----------------------------------|------|------|--------------------------|---------------------|
| Tissue Culture Water (Run 2) (Negative Control) | 100.0 | 5.63 | Non-Irritant | No Category |
| Methyl acetate (Run 2) (Positive Control) | 40.9 | 1.28 | Irritant | Category 1 or 2 |

Diff. = difference between tissues

The purpose of this study was to provide classification of chemicals concerning their eye irritation potential using an alternative to the Draize Rabbit Eye Test, according to the OECD Test Guideline No. 492, "Reconstructed Human Cornea-like Epithelium (RhCE) Test Method for Identifying Chemicals Not Requiring Classification and Labelling for Eye Irritation or Serious Eye Damage." The EpiOcular™ EIT was intended to differentiate those materials that are UN GHS No Category (i.e., do not meet the requirements for UN GHS classification) from those that would require labeling as either UN GHS Category 1 or 2.

Limitation

This assay was not intended to differentiate between UN GHS Category 1 and UN GHS Category 2 (nor between EU R36 and R41).

Table 10 lists a description of the test articles.

TABLE 10

| Identity | Description | Sample Preparation |
|----------|-------------|---------------------|
| Test Article 1: 0.073 wt % AgCNP2 in water | Clear Colorless Liquid | Used as received |
| Test Article 2: 0.01 wt % AgCNP2 in water | Clear Colorless Liquid | Used as received |

Table 11 lists a description of the Positive control and Table 12 lists a description of the Negative Control.

TABLE 11

| Positive Control | |
|------------------|---|
| Identity | Methyl acetate, Lot No. 060321JKA (Characterization not provided by supplier) |
| Storage | Room temperature and humidity |
| Description | Clear colorless |
| Provided by | MatTek Corporation |

TABLE 12

| Negative Control | |
|------------------|---|
| Identity | Tissue Culture Water, (TCH2O) Lot No. RNBJ0203 |
| Storage | Room temperature and humidity |
| Description | Clear colorless |
| Provided by | Sigma-Aldrich ® |

Plate Reader Linearity Check

The linearity of the plate reader used for optical density (OD) determination was verified prior to its use the same week the EIT assay was performed. A dilution series of trypan blue was prepared and two 200-µl aliquots per concentration were pipetted into a 96-well plate. The optical density of the plate wells was measured at a wavelength of 570 nm (OD570), with no reference wavelength. A regression line and an R-squared value were generated using Microsoft Excel® 2007. Verification was considered acceptable if the R-squared value was greater than 0.999.

Test Article Reduction of MTT

For each test article, A total of 50 μl of the test article were mixed with 1 ml of MTT solution (1 mg/ml methyl thiazole tetrazolium diluted in Dulbecco's Modified Eagle's Medium [DMEM]). A negative control (50 μl of tissue culture water, TCH2O) was tested concurrently. The solutions were incubated in the dark at 37±1° C., 5±1% CO2 for approximately 3 hours in a six-well plate. After incubation, the solutions were visually inspected for purple coloration, which indicates that the test article reduced MTT. Since tissue viability is based on MTT reduction, direct reduction by a test article can exaggerate viability, making a test article seem less irritating than its actual irritation potential. None of the test articles were found to have reduced MTT and the assay continued as per the protocol.

Assessment of Coloring or Staining Materials

The test articles 0.073 wt % AgCNP2 in water and 0.01 wt % AgCNP2 in water, were non-colored; therefore, they were assessed to determine if the extractant would become colored when mixed with the test article.

For each test article, a total of 50 μl of the test article were incubated in a six-well plate with 1 ml of TCH2O for at least 1 hour in a humidified 37±1° C., 5±1% CO2 incubator. An additional 50 μl of the test article were added to 2 ml of extractant (isopropanol) and incubated for 2 to 3 hours in a six-well plate, at room temperature with shaking. Two 200-μ aliquots of the test article plus TCH2O or test article plus extractant from each well were transferred to a 96-well plate and measured at 570 nm using a plate reader (μQuant Plate Reader, Bio-Tek Instruments, Winooski, VT). No color developed in the water or the extractant, resulting in an OD570 no more than 0.08 after subtraction of blank (TCH2O or isopropanol, respectively), so no colorant controls were added to the assay.

EpiOcular™ Tissue Samples

EpiOcular™ tissues, Lot No. 31794, Kit C and A, were received from MatTek Corporation (Ashland, MA) on 29 Jun. 2021 and refrigerated at 2 to 8° C. Before use, the tissues were incubated (37±1° C., 5±1% CO2) with assay medium (MatTek) for a 1-hour equilibration. Equilibration medium was replaced with fresh medium for an additional overnight equilibration of 16 to 24 hours. After the overnight incubation, the tissues were moistened with 20 μl of Dulbecco's phosphate-buffered saline (DPBS) and incubated at 37±1° C., 5±1% CO2 for 30±2 minutes.

Dosing

For each test article, a total of 50 μl of the test article were applied to EpiOcular™ tissues. A negative control (50 μl of TCH2O) and a positive control (50 μl of methyl acetate) were each tested concurrently. Each treatment with test article or control was conducted in duplicate. The tissues were incubated at 37±1° C., 5±1% CO2 for 30±2 minutes. After dosing and incubation, the tissues were rinsed with PBS and soaked in 5 ml of room-temperature assay medium in a 12-well plate for 12±2 minutes. The soaked tissues were then incubated in fresh assay medium at 37±1° C., 5±1% CO2 for 120±15 minutes.

Tissue Viability (MTT Reduction)

At the end of the incubation period, each EpiOcular™ tissue was transferred to a 24-well plate containing 300 μl of MTT solution (1 mg/ml MTT in DMEM). The tissues were then returned to the incubator for an MTT incubation period of 3 hours±10 minutes. Following the MTT incubation period, each EpiOcular™ tissue was rinsed with DPBS and then treated with 2.0 ml of extractant (isopropanol) in a 24-well plate overnight at room temperature in the dark allowing extraction to occur through both the top and bottom of the insert. Two 200-μl aliquots of the extracted MTT formazan from each well were transferred to a 96-well plate and measured at 570 nm using a plate reader (μQuant Plate Reader, Bio-Tek Instruments, Winooski, VT).

Analysis of Data

Viability:

See Tables 13A and 13B for Experimental Data. The mean absorbance value for each time point was calculated from the optical density (OD) of the duplicate samples and expressed as percent viability for each sample using the following formula Eq(1):

$$\% \text{ viability} = 100 \times (OD_{sample}/OD_{negative\ control}) \qquad \text{Eq (1)}$$

Quality Controls

The assay meets the acceptance criteria if the mean OD570 of the negative control tissues is greater than 0.8 and less than 2.5, and the mean relative viability of positive control tissues, expressed as percentage of the negative control tissues, is less than 50%. In addition, the difference in viability between identically treated tissues must be less than 20%.

Ocular Irritation Prediction

According to the OECD Guideline, and GHS classification, an irritant is predicted if the mean relative tissue viability of two individual tissues exposed to the test substance is ≤60% of the mean viability of the negative controls. Table 13 shows the mean tissue viability for the GHS Classification.

TABLE 13

| In Vitro Result | GHS Classification |
|---|---|
| Mean tissue viability less than or equal to 60% | Category 1 or 2 |
| Mean tissue viability greater than 60% | No Category |

If the test article-treated tissue viability is 60±5%, a second EIT should be performed. If the results of the second test disagree with the first, then a third test should be performed. The conclusion will be based on the agreement of two of the three tests.

Tables 14A and 14B show the experimental data, per test article. Table 14A shows the raw OD, the blank corrected OD data and mean of aliquots. Table 14B shows the percent viability per test article, the OD mean, OD difference, the viability % means and the viability % difference. Table 15A shows the OD blank data for run 1. Table 15B shows the OD blank data for run 2.

TABLE 14A

| Test and Control | Tissue | Raw OD data | | Blank corrected OD data | | Mean of |
|---|---|---|---|---|---|---|
| Article Identity | No. | Aliq. 1 | Aliq. 2 | Aliq. 1 | Aliq. 2 | Aliquots |
| Test Article 1: 0.073 wt % | 1 | 2.096 | 2.330 | 2.049 | 2.283 | 2.166 |
| AgCNP2 in water (Run 1) | 2 | 1.822 | 2.040 | 1.775 | 1.993 | 1.884 |
| Test Article 2: 0.01 wt % | 1 | 2.179 | 2.220 | 2.132 | 2.173 | 2.153 |
| AgCNP2 in water (Run 1) | 2 | 2.324 | 2.268 | 2.277 | 2.221 | 2.249 |
| TCH2O (Run 1) | 1 | 2.092 | 2.240 | 2.045 | 2.193 | 2.119 |
| (Negative Control) | 2 | 2.097 | 2.130 | 2.050 | 2.083 | 2.067 |
| Methyl acetate (Run 1) | 1 | 0.636 | 0.628 | 0.589 | 0.581 | 0.585 |
| (Positive Control) | 2 | 0.710 | 0.733 | 0.663 | 0.686 | 0.675 |
| TCH2O (Run 2) | 1 | 2.354 | 2.141 | 2.308 | 2.095 | 2.201 |
| (Negative Control) | 2 | 2.166 | 2.088 | 2.120 | 2.042 | 2.081 |
| Methyl acetate (Run 2) | 1 | 0.934 | 0.939 | 0.888 | 0.893 | 0.890 |
| (Positive Control) | 2 | 0.911 | 0.907 | 0.865 | 0.861 | 0.863 |

TABLE 14B

| Test and Control | Tissue | % | OD | | % Viabilities | |
|---|---|---|---|---|---|---|
| Article Identity | No. | Viability | Mean | Diff. | Mean | Diff. |
| Test Article 1: 0.073 wt % | 1 | 103.5 | 2.025 | 0.282 | 96.8 | 13.47 |
| AgCNP2 in water (Run 1) | 2 | 90.0 | | | | |
| Test Article 2: 0.01 wt % | 1 | 102.9 | 2.201 | 0.096 | 105.2 | 4.61 |
| AgCNP2 in water (Run 1) | 2 | 107.5 | | | | |
| | 2 | 9.4 | | | | |
| TCH2O (Run 1) | 1 | 101.3 | 2.093 | 0.053 | 100.0 | 2.51 |
| (Negative Control) | 2 | 98.7 | | | | |
| Methyl acetate (Run 1) | 1 | 28.0 | 0.630 | 0.089 | 30.1 | 4.28 |
| (Positive Control) | 2 | 32.2 | | | | |
| TCH2O (Run 2) | 1 | 102.8 | 2.141 | 0.121 | 100.0 | 5.63 |
| (Negative Control) | 2 | 97.2 | | | | |
| Methyl acetate (Run 2) | 1 | 41.6 | 0.877 | 0.028 | 40.9 | 1.28 |
| (Positive Control) | 2 | 40.3 | | | | |

Diff. = difference between tissues
OD = optical density

TABLE 15A

Blank Data
Run 1:

| No. | 1 | 2 | 3 | 4 | 5 | 6 | 7 | 8 | Mean |
|---|---|---|---|---|---|---|---|---|---|
| OD | 0.47 | 0.47 | 0.46 | 0.46 | 0.46 | 0.47 | 0.46 | 0.48 | 0.47 |

TABLE 15B

Run 2:

| No. | 1 | 2 | 3 | 4 | 5 | 6 | 7 | 8 | Mean |
|---|---|---|---|---|---|---|---|---|---|
| OD | 0.46 | 0.46 | 0.46 | 0.46 | 0.46 | 0.46 | 0.46 | 0.47 | 0.46 |

Quality Controls

The mean OD570 of the negative control tissues were 2.093 and 2.141, which met the acceptance criteria of greater than 0.8 and less than 2.5. The mean relative viabilities of the positive control tissues were 30.1% and 40.9%, which met the acceptance criterion of less than 50%. The differences in viability between identically treated tissues were 1.03% to 13.47%, which met the acceptance criterion of less than 20%. The R-squared value calculated for the plate reader linearity check was 0.9999, which met the acceptance criterion of greater than 0.999. All controls passed the acceptance criteria for a valid study.

Treatment/Prevention
Epithelial Tissue Wound Healing

In view of the foregoing, the embodiments herein are directed to a wound healing composition comprising metal-modified cerium oxide nanoparticles (mCNPs), as described herein, having a predominant 3+ surface charge and a tissue glue, tissue adhesive, or surgical glue, the metal-modified cerium oxide nanoparticles (mCNPs) is in an amount ranging from about 0.01-0.1% by weight and the metal is non-ionizing with antimicrobial promoting properties.

In some embodiments, the wound healing composition comprising metal-modified cerium oxide nanoparticles (mCNPs), as described herein, and a tissue glue, tissue adhesive, or surgical glue, the mCNPs to oxidize viruses and bacteria, which cause infections, but also in the presence of a healthy human cell, change its behavior to anti-oxidizing.

In some embodiments, the wound healing composition comprising metal-modified cerium oxide nanoparticles (mCNPs), as described herein, and an epithelial tissue healing agent, the mCNPs to oxidize viruses and bacteria, which cause infections, but also in the presence of a healthy human cell, change its behavior to anti-oxidizing, the mCNPs having a predominant 3+ surface charge and in an amount from about 0.01-0.1% by weight of a mixture of the epithelial tissue healing agent and the mCNPs.

The wound healing composition may include a metal selected from the group consisting of silver, gold, ruthenium, vanadium, copper, titanium, nickel, platinum, titanium, tin, zinc and iron. The metal is a stable metallic metal. The metal is a non-ionic metal with antimicrobial promoting properties.

In some embodiments, the wound healing composition comprises AgCNP2 having a predominant 3+ surface charge and in an amount of less than about 0.01 to 0.1% by weight in the wound healing composition.

The mCNPs of the wound healing composition are in the range of about 3-5 nm in size. In some embodiments, the mCNP ingredient with predominately Ce 3+ cerium oxide surface charge may have a particle size in the range of 3 nm-35 nm.

The mCNPs of the wound healing composition may comprise a predominantly 3+ cerium atom charge and a non-ionizing metal with antimicrobial properties.

The pharmaceutical acceptable composition may include an epithelial tissue healing agent selected from a group consisting of preadipocyte modulator and an adipocyte modulator and contain in a pharmaceutically acceptable composition for subcutaneous administration, and AgCNP2 having a predominant 3+ surface charge and in an amount of about 0.01 to 0.1% by weight of a mixture of the epithelial tissue healing agent and the AgCNP2.

The pharmaceutical acceptable composition may include an epithelial tissue healing agent selected from a group consisting of preadipocyte modulator and an adipocyte modulator and contain in a pharmaceutically acceptable composition for ocular tissue administration, and AgCNP2 having a predominant 3+ surface charge and in an amount of about 0.01 to 0.1% by weight.

The pharmaceutical acceptable composition may include an epithelial tissue healing agent in a pharmaceutically acceptable carrier for ocular tissue administration, and mCNPs or AgCNP2 in an amount of about 0.01 to 0.1% by weight of the epithelial tissue healing agent. The metal-modified cerium oxide nanoparticles (mCNPs) having a predominant 3+ surface charge and in a range of about 3-5 nm or 3-35 nm in size and mixed in an amount that is in a range of about 0.01 to 0.1 weight percentage of a mixture having the epithelial tissue healing agent and the mCNPs. The metal may be a non-ionizing antimicrobial promoting metal.

The pharmaceutical acceptable composition may include an epithelial tissue healing agent contain a polynucleotide in a pharmaceutically acceptable carrier for skin tissue administration, and AgCNP2 having a predominant 3+ surface charge and in an amount of about 0.01 to 0.1% by weight of the epithelial tissue healing agent. The silver is a stable metallic silver that is non-ionizing.

The pharmaceutical acceptable composition may include an epithelial tissue healing agent contain a polynucleotide in a pharmaceutically acceptable carrier for epithelial tissue administration, and AgCNP2 having a predominant 3+ surface charge and in an amount of about 0.01 to 0.1% by weight of a mixture including the epithelial tissue healing agent and the AgCNP2. The silver is a stable metallic silver that is non-ionizing.

Moreover, the method may include treating wounds with the mCNPs, described herein, and/or a wound healing composition including the mCNPs in an amount of less than about 0.01 to 0.1% by weight in the wound healing composition to assist with a body's naturally occurring processes to oxidize viruses and bacteria, which cause infections, but also in the presence of a healthy human cell, change its behavior to anti-oxidizing where the mCNPs in the wound healing composition have a predominant 3+ surface charge and are in the range of about 3-5 nm or 3-35 nm in size. The metal (m) is a non-ionizing stable metallic metal.

Moreover, the method may include treating epithelial tissue with the mCNPs, described herein, and/or a pharmaceutically acceptable composition including an epithelial tissue healing agent and the mCNPs in an amount of less than about 0.01 to 0.1% by weight in the pharmaceutically acceptable composition to assist with a body's naturally occurring processes to oxidize viruses and bacteria, which cause infections, but also in the presence of a healthy human cell, change its behavior to anti-oxidizing where the mCNPs in the wound healing composition have a predominant 3+ surface charge and are in the range of about 3-5 nm or 3-35 nm in size. The metal (m) is a non-ionizing stable metallic metal.

In some embodiments, the AgCNP2 of the wound healing composition or pharmaceutically acceptable composition for the treatment of epithelial tissue is produced via a method comprising dissolving cerium and silver precursor salts such as cerium and silver nitrates and oxidizing the dissolved cerium and silver precursor salts.

In some embodiments, the AgCNP2 of the wound healing composition or pharmaceutically acceptable composition for the treatment of epithelial tissue is produced via a method comprising dissolving cerium and silver precursor salts such as cerium and silver nitrates; oxidizing the dissolved cerium and silver precursor salts via admixture with peroxide; and precipitating nanoparticles by subjecting the admixture with ammonium hydroxide.

In some embodiments, the AgCNP2 of the wound healing composition or pharmaceutically acceptable composition is produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver where the mCNPs in the wound healing composition have a predominant 3+ surface charge and are in the range of about 3-5 nm or 3-35 nm in size.

In some embodiments, the AgCNP2 of the pharmaceutically acceptable composition is produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver where the mCNPs in the wound healing composition have a predominant 3+ surface charge and are in the range of about 3-5 nm or 3-35 nm in size.

In some embodiments, a method is provided of inducing or accelerating a healing process of a damaged skin or skin wound, by administering to the skin cells colonizing the damaged skin or skin wound area a therapeutically effective amount of a wound healing composition including AgCNP2 and a viral vector comprising a polynucleotide coding for an adipokine, thus transforming said skin cells to express and secrete said adipokine, thereby inducing or accelerating the healing process of the damaged skin or skin wound, where the AgCNP2 has a predominant 3+ surface charge and a size in the range of about 3-5 nm or 3-25 nm and in an amount of 0.01 to 0.1 wt. % of the wound healing composite to assist with a body's naturally occurring processes to oxidize viruses and bacteria, which cause infections, but also in the presence of a healthy human cell, change its behavior to anti-oxidizing. The silver (Ag) is a stable metallic silver that is non-ionizing.

In some embodiments, a wound healing composition includes a viral vector comprising polynucleotide coding for an adipokine, to transform skin cells to express and secrete adipokine and AgCNP2 having a predominant 3+ surface charge and a size in the range of about 3-5 nm or 3-35 nm and in an amount of 0.01 to 0.1 wt. % of the wound healing composite to assist with a body's naturally occurring processes to oxidize viruses and bacteria, which cause infections, but also in the presence of a healthy human cell, change its behavior to anti-oxidizing.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

Embodiments are described herein with reference to the attached figures wherein like reference numerals are used throughout the figures to designate similar or equivalent elements. In some instances, figures are not drawn to scale and they are provided merely to illustrate aspects disclosed herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Therefore, the breadth and scope of the subject matter provided herein should not be limited by any of the above explicitly described embodiments. Rather, the scope of the embodiments should be defined in accordance with the following claims and their equivalents.

What is claimed is:

1. A therapeutic article of manufacture comprising:
a body having fibers treated with a mixture including metal-modified cerium oxide nanoparticles (mCNPs) having a predominant 3+ surface charge and in a range of about 3-35 nanometers (nm) in size and one or more of a polymeric binder, a dispersant, a stabilizer or combinations thereof, the mCNPs are mixed in an amount that is in a range of about 0.01 to 0.1 weight percentage of the mixture and m is an antimicrobial promoting metal that is non-ionizing wherein the body further includes an anti-inflammatory dressing or an analgesic dressing, and wherein the mCNPs consist of AgCNP2 and the metal is a stable metallic silver that is non-ionizing and a Janus-type two-phase construct.

2. The therapeutic article of manufacture according to claim 1, wherein the fibers include one or more of polymers, yarns, cotton, synthetic polymer fibers or combinations thereof.

3. The therapeutic article of manufacture according to claim 1, wherein the body further comprises:
a first layer including the treated fibers;
a second layer including a waterproof layer having a first side and a second side; and
a high-grab and/or instant tack adhesive on the second side.

4. The therapeutic article of manufacture according to claim 3, further comprising a third layer of at least one peel-off liner overlaying the treated fibers and the high-grab and/or instant tack adhesive.

5. The therapeutic article of manufacture according to claim 1, wherein the therapeutic article comprises additional mCNPs and the metal (m) of the additional mCNPs is selected from the group consisting of silver, gold, ruthenium, vanadium, copper, titanium, nickel, platinum, tin, zinc or iron.

6. The therapeutic article of manufacture according to claim 1, wherein the mixture includes the polymeric binder, the dispersant and the stabilizer and the dispersant and the stabilizer promote adhesion with the polymeric binder and the fibers.

7. The therapeutic article of manufacture according to claim 1, wherein the body further includes biological or naturally derived agents.

8. The therapeutic article of manufacture according to claim 1, wherein the body further includes a surgical wound dressing form factor.

9. The therapeutic article of manufacture according to claim 1, wherein:
the mixture further includes a therapeutic dosage of epithelial tissue healing agent; and
the treated fibers are impregnated fibers impregnated with or formed of the mixture.

10. The therapeutic article of manufacture according to claim 9, wherein the body further comprises a non-adherent semipermeable membrane or non-adherent porous material on top of and surrounding the treated fibers, so that the therapeutic dosage of epithelial tissue healing agent is dispensed through the non-adherent semipermeable membrane or the non-adherent porous material.

11. The therapeutic article of manufacture according to claim 1, wherein the treated fibers eradicate Rhinovirus 14, SARS-COV-2 surrogate OC43 coronavirus and Parainfluenza virus type 5 trapped by the fibers.

12. The therapeutic article of manufacture according to claim 1, wherein the treated fibers eradicate *Streptococcus mutans* and *Staphylococcus aureus* trapped by the treated fibers.

13. A method comprising:
applying a barrier using a therapeutic article of manufacture of claim 1, over a portion of an anatomical body part to protect the portion of the anatomical body part;
trapping, by the barrier, at least one of a bacteria or virus to treat the at least one bacteria or virus by the barrier; and
eradicating, by the barrier, the at least one of the bacteria and virus.

14. The method according to claim 13, wherein the virus includes at least one of Rhinovirus 14, SARS-COV-2 surrogate OC43 coronavirus or Parainfluenza virus type 5.

15. The method according to claim 13, wherein the portion of the anatomical body part includes a wound, incision or laceration.

16. The method according to claim 13, wherein the applying of the barrier includes adhesively affixing the therapeutic article of manufacture with a high-grab and/or instant tack adhesive to skin of the portion of the anatomical body part.

17. The method according to claim 13, wherein the bacteria includes at least one of *Streptococcus mutans* or *Staphylococcus aureus*.

18. The method according to claim 13, wherein the mixture of the therapeutic article of manufacture includes a therapeutic dosage of epithelial tissue healing agent; and treated fibers of the therapeutic article of manufacture are impregnated fibers impregnated with or formed of the mixture.

19. The method according to claim 13, wherein the mixture of the therapeutic article of manufacture includes a polymeric binder, a dispersant and a stabilizer and the dispersant and the stabilizer promote adhesion with the polymeric binder and fibers of a body of the therapeutic article of manufacture.

* * * * *